(12) United States Patent
Holman et al.

(10) Patent No.: US 8,192,456 B2
(45) Date of Patent: Jun. 5, 2012

(54) METAL VASCULAR APERTURE CLOSURE DEVICE

(75) Inventors: Tom Holman, Princeton, MN (US); Jeff Welch, Maple Grove, MN (US); Howard Root, Excelsior, MN (US)

(73) Assignee: Vascular Solutions, Inc., Minneapolis, MN (US)

( * ) Notice: Subject to any disclaimer, the term of this patent is extended or adjusted under 35 U.S.C. 154(b) by 410 days.

(21) Appl. No.: 12/501,998

(22) Filed: Jul. 13, 2009

(65) Prior Publication Data

US 2011/0009900 A1  Jan. 13, 2011

(51) Int. Cl.
*A61B 17/08* (2006.01)
*A61D 1/00* (2006.01)

(52) U.S. Cl. ........ 606/213; 606/151; 606/215; 606/232; 623/1.11

(58) Field of Classification Search ............... 606/151, 606/213, 215, 232; 623/1.11
See application file for complete search history.

(56) References Cited

U.S. PATENT DOCUMENTS

| | | | |
|---|---|---|---|
| 3,874,388 A | 4/1975 | King et al. |
| 4,614,945 A | 9/1986 | Brunius et al. |
| 4,669,473 A | 6/1987 | Richards et al. |
| 4,744,364 A | 5/1988 | Kensey |
| 4,852,568 A | 8/1989 | Kensey |
| 4,890,612 A | 1/1990 | Kensey |
| 5,021,059 A | 6/1991 | Kensey et al. |
| 5,061,274 A | 10/1991 | Kensey |
| 5,108,421 A | 4/1992 | Fowler |
| 5,192,300 A | 3/1993 | Fowler |
| 5,192,301 A | 3/1993 | Kamiya et al. |
| 5,192,302 A | 3/1993 | Kensey et al. |
| 5,222,974 A | 6/1993 | Kensey et al. |
| 5,272,616 A | 12/1993 | Divan et al. |
| 5,275,616 A | 1/1994 | Fowler |
| 5,282,827 A | 2/1994 | Kensey et al. |
| 5,312,435 A | 5/1994 | Nash et al. |
| 5,318,040 A | 6/1994 | Kensey et al. |
| 5,324,306 A | 6/1994 | Makower et al. |

(Continued)

FOREIGN PATENT DOCUMENTS

DE  2 333 03 A1  2/1986

(Continued)

OTHER PUBLICATIONS

U.S. Appl. No. 12/502,034, filed Jul. 13, 2009, Tom Holman et al.

*Primary Examiner* — Vy Q Bui
(74) *Attorney, Agent, or Firm* — Patterson Thuente Christensen Pedersen, P.A.

(57) ABSTRACT

A closure device to be inserted at least partially through a blood vessel wall aperture in a blood vessel wall, having at least two metal petals that can be inserted through the blood vessel wall aperture and into the lumen of the blood vessel. The petals are structured to prevent withdrawal through the blood vessel wall aperture when the length of the petal is generally aligned with the blood vessel wall. The metal petals have alignment features that tend to urge them into alignment relative to each other. The closure device includes a metal expansion member that is alterable from an unexpanded state to an expanded state. A bioabsorbable tensioning member interconnects the petals and the metal expansion member and is securable to the metal expansion member.

22 Claims, 25 Drawing Sheets

U.S. PATENT DOCUMENTS

| | | | |
|---|---|---|---|
| 5,342,393 A | 8/1994 | Stack | |
| 5,350,399 A | 9/1994 | Erlebacher et al. | |
| 5,383,886 A | 1/1995 | Kensey | |
| 5,383,897 A | 1/1995 | Wholey | |
| RE34,866 E | 2/1995 | Kensey et al. | |
| 5,391,183 A | 2/1995 | Janzen et al. | |
| 5,403,278 A | 4/1995 | Ernst et al. | |
| 5,411,520 A | 5/1995 | Nash et al. | |
| 5,437,631 A | 8/1995 | Janzen | |
| 5,441,517 A | 8/1995 | Kensey et al. | |
| 5,454,833 A | 10/1995 | Boussignac et al. | |
| 5,478,352 A | 12/1995 | Fowler | |
| 5,507,744 A | 4/1996 | Tay et al. | |
| 5,523,291 A | 6/1996 | Janzen et al. | |
| 5,531,757 A | 7/1996 | Kensey et al. | |
| 5,531,759 A | 7/1996 | Kensey | |
| 5,545,178 A | 8/1996 | Kensey et al. | |
| 5,549,633 A | 8/1996 | Evans et al. | |
| 5,591,204 A | 1/1997 | Janzen et al. | |
| 5,591,205 A | 1/1997 | Fowler | |
| 5,593,422 A | 1/1997 | Muijs Van de Moer | |
| 5,601,602 A | 2/1997 | Fowler | |
| 5,620,461 A | 4/1997 | Muijs Van de Moer | |
| 5,643,317 A | 7/1997 | Pavcnik et al. | |
| 5,645,566 A | 7/1997 | Brenneman et al. | |
| 5,649,959 A | 7/1997 | Hannam et al. | |
| 5,662,681 A | 9/1997 | Nash et al. | |
| 5,676,689 A | 10/1997 | Kensey et al. | |
| 5,676,698 A | 10/1997 | Janzen et al. | |
| 5,681,334 A | 10/1997 | Evans et al. | |
| 5,690,674 A | 11/1997 | Diaz | |
| 5,700,277 A | 12/1997 | Nash et al. | |
| 5,705,488 A | 1/1998 | Janzen et al. | |
| 5,707,393 A | 1/1998 | Kensey et al. | |
| 5,716,375 A | 2/1998 | Fowler | |
| 5,725,498 A | 3/1998 | Janzen et al. | |
| 5,725,521 A | 3/1998 | Mueller | |
| 5,728,114 A | 3/1998 | Evans et al. | |
| 5,741,223 A | 4/1998 | Janzen et al. | |
| 5,746,755 A | 5/1998 | Wood et al. | |
| 5,782,860 A | 7/1998 | Epstein et al. | |
| 5,810,810 A | 9/1998 | Tay et al. | |
| 5,830,130 A | 11/1998 | Janzen et al. | |
| 5,861,004 A | 1/1999 | Kensey et al. | |
| 5,916,236 A | 6/1999 | Muijs Van de Moer | |
| 5,922,009 A | 7/1999 | Epstein et al. | |
| 5,922,024 A | 7/1999 | Janzen et al. | |
| 5,935,147 A | 8/1999 | Kensey et al. | |
| 5,947,997 A | 9/1999 | Pavcnik et al. | |
| 5,948,425 A | 9/1999 | Janzen | |
| 5,951,589 A | 9/1999 | Epstein et al. | |
| 6,007,563 A | 12/1999 | Nash et al. | |
| 6,045,569 A | 4/2000 | Kensey et al. | |
| 6,063,085 A | 5/2000 | Tay et al. | |
| 6,090,130 A | 7/2000 | Nash et al. | |
| 6,162,192 A | 12/2000 | Cragg et al. | |
| 6,179,863 B1 | 1/2001 | Kensey et al. | |
| 6,190,400 B1 | 2/2001 | Van de Moer | |
| 6,325,789 B1 | 12/2001 | Janzen et al. | |
| 6,334,865 B1 | 1/2002 | Redmond et al. | |
| 6,764,500 B1 | 7/2004 | Muijs Van de Moer | |
| 7,008,439 B1 | 3/2006 | Janzen et al. | |
| 7,169,168 B2 | 1/2007 | Muijs Van de Moer et al. | |
| 2001/0003158 A1 | 6/2001 | Kensey et al. | |
| 2007/0135842 A1 | 6/2007 | Muijs Van de Moer et al. | |
| 2007/0244518 A1* | 10/2007 | Callaghan | 606/215 |

FOREIGN PATENT DOCUMENTS

| | | |
|---|---|---|
| FR | 2 607 706 | 6/1988 |
| SU | 1 055 520 A | 11/1983 |
| SU | 1 088 709 A | 4/1984 |

* cited by examiner

METAL VASCULAR APERTURE CLOSURE DEVICE

FIELD OF THE INVENTION

The invention relates generally to the closure of punctures blood vessel walls during catheter based intravascular surgical procedures. More specifically, the invention relates to sutureless closure of wounds created in blood vessel walls in intravascular surgery and joining the wound edges without stitching the edges together.

BACKGROUND OF THE INVENTION

Many medical procedures involve accessing blood vessels in and around the heart, often by making an incision, puncture or other aperture in the femoral artery in the area of the groin or upper thigh and inserting a medical device into and up through the femoral artery. Access may also be gained via other major arteries in the body. For the purposes of this application, a puncture as discussed should be considered to include an incision, slit or circular opening that passes through the wall of a blood vessel. The terms blood vessel wall aperture, wound aperture, puncture and incision are not to be considered to be limited to any particular shape of opening. A blood vessel wall aperture, puncture or incision includes any opening made in a blood vessel wall or the wall of another bodily organ. This may include but is not limited to surgical incisions, punctures made by needles and openings created with a trephine.

Once the medical procedure is completed, an aperture is left in the wall of the artery or vein that has been accessed. These apertures tend to bleed, particularly in the case of arterial punctures because of the higher arterial blood pressure as compared to the venous blood pressure. To stop bleeding in these situations, it is common for medical personnel to hold pressure on the punctured arterial or venous wall for a substantial period of time after the medical instruments are withdrawn. It is commonly required to hold pressure on the puncture wound for 15 to 30 minutes to stop bleeding. If the patient has been treated with large amounts of anti-coagulant medication, the time required for applying pressure to cause clotting at the puncture site may be substantially extended.

After bleeding has stopped an elastic pressure bandage is typically applied over the site of the puncture to exert pressure on the site in an attempt to prevent the blood clot from being dislodged by blood flow within the blood vessel. With this scenario, it is often necessary for the pressure bandage to remain in place from 8 to 24 hours. Often, the use of a pressure bandage prevents ambulation of the patient and requires that the patient remain resting in bed.

Various attempts have been made to address this problem by suturing closed the aperture or by blocking or sealing the aperture with structures that are either inserted into the blood vessel puncture or applied just external to the blood vessel at the aperture site.

Prior art efforts to address this problem have included suture devices, which do not provide a complete closure or seal of the puncture wound such as the Perclose device. Also used have been staple based devices such as the Starclose device, which attempts to pinch the vessel puncture closed. Other devices have utilized balloons or toggle bolt like structures in an effort to close the puncture wound left behind after intravascular procedures.

Unfortunately, none of these prior art devices has been as successful as would be desired. As such, there is still room for improvement in such vascular closure techniques.

SUMMARY OF THE INVENTION

The absorbable metal closure device of the present invention solves many of the problems and makes improvements over the prior art. The absorbable metal closure device of the invention generally includes an internal member, an external member and a filament.

The internal member is adapted to be inserted percutaneously through a puncture wound in a blood vessel wall into the lumen of the blood vessel. In an example embodiment, the internal member generally includes two or more petals. In one example embodiment, there are three petals. In an example embodiment, the petals are flat members formed of magnesium and each of the petals is centrally pierced by at least two apertures. In an example embodiment including two petals, the apertures are oriented to be aligned approximately 90° from each other relative to the short axis of the petals. Other features may be used to urge the petals into desired alignment upon deployment into the blood vessel lumen. For example, the features may include a single aperture in each petal or ridges that urge the petals into the desired alignment. In an alternate example embodiment at least some of the petals can be permitted to rotate freely relative to other petals to take random angular orientations relative to the other petals.

In another example embodiment including three petals, the apertures are aligned in one petal at approximately thirty degrees relative to the short axis and another petal at approximately ninety degrees relative to short axis and a third petal at approximately one hundred fifty degrees to the short axis.

In another example embodiment including three petals, the apertures are aligned in one petal at approximately zero degrees relative to the short axis and another petal at approximately 60° relative to short axis and a third petal at approximately 120° to the short axis.

The apertures are aligned relative to the petals so that when the apertures are brought into alignment by passing another structure through them, such as a filament, the petals are drawn into a particular alignment relative to each other which is expanded relative to the width of any individual petal. Thus, the two metal petals cover a surface area greater than either of the metal petals alone.

The three petals are adapted to be aligned generally parallel to one another prior to insertion and are dimensioned so as to be passable through the aperture when aligned.

In another example embodiment, one of the petals has one or two small apertures centrally locate therein and a second and further petals located proximal to the first petal have a single larger aperture centrally located. In this embodiment, the second and further petals rotate freely relative to the first petal and settle into random angular orientations relative to the first petal when freed from the confines of a delivery device into a blood vessel lumen.

In another example embodiment, one or more of the petals presents a recess or pocket into which a buffer, as described elsewhere in this application, may be inserted. The pocket may be located centrally in the petal so as to be hidden or covered by the overlap of other adjacent petals.

An example external member generally includes a stem portion, an expandable retainer portion and a locking part.

The stem, in one example embodiment, is a generally cylindrical structure that has a length and diameter that allows it to fit within the blood vessel wall aperture. The stem also defines passages therethrough sized to receive the filament therethrough. The stem is arranged so that its internal face abuts the petals when the petals are drawn against it by the filament. The stem also has an external face adapted to abut the expandable retainer portion when the filament is tensioned.

In one embodiment of the invention, the external face of the stem is permanently secured to the expandable retainer portion.

The expandable retainer portion generally includes a distal portion, a proximal portion and an expansion portion.

The distal portion in one example embodiment may be generally cylindrical and adapted to abut the external face of the stem.

The proximal portion may also be substantially cylindrical in shape.

In one example embodiment, the expansion portion is structured so that it can be expanded by deformation of the metal so as to be shiftable from an unexpanded configuration to an expanded configuration. In one example embodiment, the expansion is accomplished by tensioning the filament to compress the proximal portion toward the distal portion. In one example embodiment, the diameter of the expandable retainer, when unexpanded, is about equal to the petal width and to the spacer diameter. When in the expanded configuration, the expandable retainer may have a greatest extent equal to approximately 3 to 4 times the spacer diameter. As such, the expanded extent is also approximately 3 to 4 times the greatest dimension of the puncture wound in the blood vessel wall.

The locking part, in an example embodiment, includes a cam or wedge that immovably secures the filament after it has been placed under tension so that it will remain under tension and not be released.

In one example embodiment, the locking part may include a disc having three apertures in it about which the filament may be passed in order to create a knot to secure the filament to the locking part.

In another example embodiment, the locking part may include a wedge or cam which can be pressed into a receiver so as to entrap the filament between the wedge and the receiver and secure it by friction and compression.

In another example embodiment, the locking part includes deformable parts that can be deformed to collapse inwardly to entrap the filament between the deformable parts and thus grip the filament to secure it against longitudinal movement. These examples should not be considered limiting as many types of locking parts may be used.

In another example embodiment, the external member may include a metal coiled member. During placement the coiled member is stretched longitudinally along a linear member. The coiled member is expanded by compressing it longitudinally while expanding it into disc like configuration transversely. The transverse extent of the disc like configuration can be varied by twisting the coiled member relative to the linear member. A tighter twist leads to a lesser transverse extent or diameter while a looser twist leads to a greater transverse extent or diameter. The disc like coiled member can be placed near or against the exterior of the blood vessel wall and expanded to substantially secure its position relative to the blood vessel wall In another example embodiment, the external member may include a deformable structure that can be deformed from a generally linear configuration to an expanded orientation wherein the deformable structure assumes, for example a bowtie orientation. In one example, the deformable structure has several apertures therein through which the filament passes and several twisted portions and/or portions having a reduced cross sectional area that facilitate folding of the deformable structure.

In another example embodiment, the external member may include a metal deformable member that includes fingers or claws that can be actuated to deform inwardly and grip tissue near the blood vessel wall or grip the blood vessel wall itself. This embodiment may include a sliding external sleeve that can be advanced at least partially over the fingers or claws to urge them inwardly to facilitate the tissue gripping action. The inward deformation may also lead to gripping of the filament within the external member structure to secure the movement of the filament relative to the external member and to secure the external member relative to the internal member via the intervening filament.

The filament may, for example, be formed from an absorbable suture material. The filament, in an example embodiment, is looped so that each of its free ends passes through the apertures in each of the petals, through the stem, through the expandable retainer, through the locking part and extends beyond the absorbable metal closure device having sufficient length to be passed well outside the tissue tract leading from the blood vessel wall puncture to the skin and outside of the body when the closure device is inserted into a puncture wound in a blood vessel.

The biodegradable metal closure device, in an example embodiment, is formed of an alkaline earth metal, such as magnesium (atomic number 12) or a rare earth element such as dysprosium (atomic number 66.) In one example embodiment, the absorbable metal closure device is formed of magnesium that has been refined to be 99.8% pure magnesium. The 0.20% includes normally present impurities in the metal. In another example embodiment, the absorbable metal closure device is formed of magnesium that is between 90.00% and 99.99% pure.

It has been found that the 99.8% pure magnesium degrades rapidly at a pH of approximately 7.4 to 7.6. This pH is common within the human body.

Experiments have demonstrated that it is possible to alter the time required for dissolution of the magnesium by altering the surface topography of the magnesium parts by particulate blasting them to roughen the surface thus increasing the surface area. Three example particulates that have been used for surface blasting are aluminum oxide ($AL_2O_3$), Magnesium Oxide (MgO) or silicon carbide (SiC). It one example embodiment, making the petals to have a thickness of between 0.003 and 0.005 of an inch, has been found to be appropriate.

It has been found that magnesium possesses anti-inflammatory properties as well as properties that promote endothelial cell adherence which are expected to facilitate biological repair of an aperture in which the metal closure device is located in an implanted environment.

In an example embodiment, the absorbable metal closure device of the invention can be passed through an introducer sheath that is already in a tissue tract from the puncture and medical procedure. For passage through the introducer sheath, the absorbable metal closure device can be arranged so that the filament is slack and the petals are aligned to be generally parallel with their long axes aligned generally parallel with the long axis of the introducer sheath. The petals are followed in the introducer sheath by the stem and then the retainer in an unexpanded state. The filaments then trail behind the retainer up through the length of the introducer to a location outside of the body.

The absorbable metal closure device can be pushed through the sheath by the use of a deployment tube formed of, for example, a polymer material such as Poly[aryl ether ether ketone] (PEEK.)

The filament may be routed through the lumen of the deployment tube. After the absorbable metal closure device has been advanced through the delivery tube by pushing it with the deployment tube and at least partially into the lumen of the blood vessel through the puncture wound, the filament may be tensioned to cause the petals to align based on the orientation of the apertures through the petals through which the filament passes. In an example embodiment having three petals, this would cause the three petals to be aligned so that their long axes are at 0, 60 and 120 degrees relative to one another. In another example embodiment, the filament has a resiliency such that when the petals are free of the delivery tube in the blood stream the resiliency of the filament tends to urge the petals toward a fanned out orientation relative to each other. As the filament is tensioned, the petals are also are drawn up against and abutting the stem which in turn abuts the retainer portion. The delivery tube and/or filament can then be withdrawn until the petals are pressed against the inner wall of the blood vessel in an abutting relationship. Once this positioning is achieved, additional tension may be applied to the filament in combination with an advancing force being applied to the delivery tube which in turn causes the deformation of the expansion portion of the expandable retainer causing the deformed metal portions to extend outward while the proximal portion and the distal portion of the expandable retainer approach one another.

The expandable retainer has at least two portions that expand outward. In one example embodiment, four expandable portions are present. In another example embodiment, six expandable portions are present After the expandable retainers expand to the desired degree, the locking portion may be actuated to secure the filament against the expansion portion thereby securing the filament under tension from the petals back to the expansion portion. Once the filament is secured by, for example, friction and compression, the filament may be severed and the delivery tube may be removed from the tissue tract. At this point, the combination of the petals, stem and retainer inhibit the flow of blood out of the blood vessel and into the surrounding tissues or tissue tract. As such, the absorbable metal closure device provides a relative seal against leakage from the blood vessel.

Outward expansion of the retainer portion expands into the tissue tract to grip the surrounding muscle, fascia and connected tissue. In some embodiments of the invention, the retainer portion may make contact with the exterior of the blood vessel wall.

Upon being left in situ in a living being such as within the human body, the petals, stem and expandable retainer dissolve by a process of steady state hydrogen evolution and gradually biodegrade within a living being in a period of time that permits biological repair of the blood vessel wall. The absorbable suture which is formed, for example, of polysorb, cat gut or other absorbable suture materials dissolves as well.

In one example embodiment, the petals have a length of about six millimeters, a width of about two millimeters and a thickness of about five thousands of an inch.

The stem is adapted to fit into the blood vessel wall aperture and contributes substantially to inhibiting blood leakage through the aperture. In one example embodiment the stem is about two mm in length and approximately two mm in diameter.

It is has been observed that the blasting of the parts of the absorbable metal closure device with aluminum oxide increases the electrolytic action and speeds dissolution of the magnesium, likely because of dissimilar metal corrosion. It has also been observed that it is possible to titrate or control the dissolution time of the magnesium by appropriate treatment with particulate blasting.

In another aspect of the invention, the surface of the metal parts of the invention may be modified, for example by particulate blasting, application of a coating or addition of a discrete additional component to introduce an acidic buffer to the absorbable metal closure device. The acidic buffer functions to maintain the pH in the vicinity of the absorbable metal closure device below a critical level. For example, for a magnesium device the buffer maintains the pH below eight. It has been observed that in an environment having a pH of about eight or above the magnesium in an example embodiment no longer dissolves.

It has also been observed that at least some of the time white blood cells in the blood stream may at least partially encapsulate portions of the absorbable metal closure device that are in the lumen of the blood vessel creating a pocket in the vessel that limits blood flow near the device. As the magnesium dissolves, the pH surrounding the device may rise and slow dissolution. The buffer should tend to counteract the rise in pH. Similarly, portions of the absorbable metal closure device located outside of the blood vessel wall may be located in tissues that have limited blood flow. This may allow the pH to rise and hinder dissolution. Thus, the buffer is expected to assist in controlling the rate of dissolution by preventing elevated pH from slowing the dissolution process.

It is expected that one embodiment of the invention will show about two weeks dissolution time in the artery itself and two weeks dissolution time for the portion located outside the artery.

The invention also includes a method of providing a device to close a blood vessel wall aperture. The method includes supplying a vascular closure device as described herein and providing instructions for the use of the vascular closure device as describe herein.

In one example embodiment the invention includes a closure device to be inserted at least partially through a blood vessel wall aperture in a blood vessel wall, the blood vessel having a lumen, the closure device comprising:

at least two metal petals, each petal having a length, a width and a thickness, the width and thickness being such that the at least two metal petals can be inserted through the blood vessel wall aperture and into the lumen of the blood vessel, the length and the width being such that the length and the width prevent withdrawal of the at least two metal petals from the blood vessel through the blood vessel wall aperture when the length of at least one of the two metal petals is generally aligned with the blood vessel wall, the at least two metal petals having alignment features that tend to urge the at least two metal petals into alignment relative to each other;

a metal expansion member that is alterable from an unexpanded state to an expanded state, which, when in the unexpanded state, is advanceable to a location near the blood vessel wall and which when in the expanded state is limited in movement relative to the blood vessel wall; and a bioabsorbable tensioning member that interconnects the at least two metal petals and the metal expansion member and that draws the petals and the metal expansion member toward each other upon being tensioned and that is securable to the metal expansion member to substantially maintain a relative positional relationship between the at least two metal petals and the metal expansion member upon being secured, whereby the at least two metal petals are positionable in the lumen adjacent to the blood vessel wall and the metal expansion member is limited in movement relative to the at least two metal petals and the at least two metal petals are stabilized in the blood vessel.

In another example embodiment, the metal biodegrades within a living being in a period of time that permits biological repair of the blood vessel wall in and around the blood vessel aperture.

In another example embodiment, a surface topography of at least one of the metal expansion member or the at least two metal petals is modified whereby biodegradation of at least part of the closure device is facilitated.

In another example embodiment, the invention includes a buffer whereby pH near at least part of the closure device is affected and whereby biodegradation of at least part of the closure device is facilitated.

In another example embodiment, the invention includes a metal stem portion having a cross sectional dimension to fit within the blood vessel wall aperture in a relationship that inhibits the passage of fluid through the blood vessel wall aperture, the stem portion being located between the at least two petals and the expansion member.

In another example embodiment, the bioabsorbable tensioning member comprises a filament that passes through each of the at least two metal petals and the expansion member and interfaces with the at least two metal petals in such a way that when the filament is tensioned the at least two metal petals are urged into an alignment wherein the length of the at least two metal petals is nonparallel.

In another example embodiment, the alignment features comprise two apertures located in each of the at least two metal petals and the two apertures are differently oriented in each of the at least two metal petals such that when the apertures are aligned the at least two petals are offset from each other at angular intervals.

In another example embodiment, the alignment features include an aperture located in each of the at least two metal petals.

In another example embodiment, the expansion member includes a generally tubular structure having a deformable portion that deforms transversely upon longitudinal compression of the expansion member.

In another example embodiment, the invention includes a locking portion that selectively secures the bioabsorbable tensioning member so that movement of the bioabsorbable tensioning member relative to the metal expansion member is inhibited.

In another example embodiment, the locking mechanism further includes a wedge and a wedge receiver that the bioabsorbable tensioning member passes between, the wedge and the wedge receiver being shiftable relative to one another between a disengaged state and an engaged state, the disengaged state being such that the bioabsorbable tensioning member is movable relative to the metal expansion member, the engaged state being such that the bioabsorbable tensioning member is secured between the wedge and the wedge receiver to inhibit movement of the bioabsorbable tensioning member relative to the expansion member.

In another example embodiment, the wedge, the wedge receiver or both are formed of metal.

In another example embodiment, the metal consists essentially of magnesium.

In another example embodiment, the invention includes an insertion assembly, the insertion assembly comprising a bypass tube, a delivery tube and a deployment tube.

In another example embodiment, the deployment tube further comprising an engagement feature at the distal end thereof, the engagement feature being structured to engage the metal expansion member and the deployment tube being structured to receive the bioabsorbable tensioning member therethrough, wherein the bioabsorbable tensioning member is movable through the deployment tube.

In another example embodiment, the metal consists essentially of magnesium.

In another example embodiment, the magnesium has a purity in a range from about 90.0 percent to about 99.99 percent.

In another example embodiment, the magnesium is about 99.80 percent pure.

In another example embodiment, the metal comprises magnesium alloyed with another metal.

In another example embodiment, the magnesium is alloyed with iron.

In another example embodiment, the magnesium is alloyed with manganese.

In another example embodiment, the invention includes method of substantially blocking fluid leakage from a blood vessel aperture in a blood vessel wall that exists in a blood vessel having a lumen, the method comprising: inserting a closure device at least partially through the blood vessel wall aperture, advancing a first metal portion of the closure device through the blood vessel aperture into the lumen, the first metal portion having at least two parts and manipulating the at least two parts of the first metal portion such that the first metal portion is oriented against the blood vessel wall within the lumen and the at least two parts resist exiting the blood vessel through the blood vessel aperture; advancing a second metal portion of the closure device until the second metal portion is near the blood vessel; wall; altering the second metal portion to expand transversely to substantially secure the second metal portion outside the blood vessel wall; pulling the first metal portion with a bioabsorbable tensioning member while shifting the second metal portion to a position closer to the first metal portion and to the blood vessel wall while expanding the second metal portion transversely; and securing the bioabsorbable tensioning member under tension such that the first metal portion and the second metal portion are substantially fixed relative to each other.

In another example embodiment, the invention includes selecting the metal such that the metal biodegrades within a living being in a period of time that permits biological repair in and around the blood vessel wall.

In another example embodiment, the invention includes inserting a third metal portion into the blood vessel wall aperture between the first metal portion and the second metal portion, the third metal portion having a cross sectional dimension to fit within the blood vessel wall aperture whereby passage of fluid through the blood vessel wall aperture is inhibited.

In another example embodiment, the first metal portion includes at least two metal petals and further comprising interfacing the bioabsorbable tensioning member with the at least two metal petals such that when the bioabsorbable tensioning member is tensioned the at least two metal petals are urged into an alignment wherein the length of petals is oriented at a relative angle and wherein the at least two metal petals cover a surface area greater than either of the at least two metal petals alone.

In another example embodiment, the invention includes providing the first portion such that it includes at least two metal petals each comprising alignment features; and tensioning the bioabsorbable tensioning member to urge the alignment features into alignment such that the at least two petals are offset from each other at angular intervals.

In another example embodiment, the invention includes providing the first portion such that it includes at least two metal petals each having two apertures located therein; and tensioning the bioabsorbable tensioning member to urge the two apertures into alignment such that the at least two petals are offset from each other at angular intervals.

In another example embodiment, the invention includes deforming the second metal portion by compressing a proximal portion of the second metal portion toward a distal portion of the second metal portion to shorten an axial length of the second metal portion while expanding the second metal portion transversely.

In another example embodiment, the invention includes selectively securing the bioabsorbable tensioning member so that relative movement of the bioabsorbable tensioning member, the first metal portion and the second metal is inhibited.

In another example embodiment, the invention includes applying a distal directed force to the second metal portion while tensioning the bioabsorbable tensioning member to secure the first metal portion, the second metal portion and the bioabsorbable tensioning member such that movement of the first metal portion, the second metal portion and the bioabsorbable tensioning member relative to each other is inhibited.

In another example embodiment, the invention includes applying a distal directed force to the second metal portion while tensioning the bioabsorbable tensioning member to expand the second metal portion transversely.

In one example embodiment the invention includes a closure device to be inserted at least partially through a blood vessel wall aperture in a blood vessel wall, the blood vessel having a lumen, the closure device comprising:

at least two parts, including an internal part and an external part, the internal part being adapted to be extended at least partially through the blood vessel wall aperture and into the lumen to at least partially block the blood vessel wall aperture, each of the internal part and the external part consisting essentially of a metal that biodegrades within a living being in a period of time that permits biological repair of the blood vessel wall in and around the blood vessel wall and at least the external part being movable relative to the internal part.

In one example embodiment, the metal is magnesium.

In one example embodiment, the magnesium has a purity in a range from about 90.0 percent to about 99.99 percent.

In one example embodiment, the magnesium is about 99.80 percent pure.

In one example embodiment, at least one of the two parts has had its surface topography altered whereby biodegradation of at least part the closure device is facilitated.

In one example embodiment, the surface topography has been altered by particulate blasting whereby biodegradation of at least part the closure device is facilitated.

In one example embodiment, the invention includes a buffer whereby pH near at least part of the closure device is affected and whereby biodegradation of at least part the closure device is facilitated.

In one example embodiment, the magnesium is alloyed with another metal.

In another example embodiment, the other metal comprises iron.

In one example embodiment, the other metal comprises manganese.

In one example embodiment, the invention includes method of substantially blocking fluid leakage from an aperture in a blood vessel wall of a blood vessel, the blood vessel having a lumen, the method comprising:

inserting a device at least partially into the blood vessel aperture, the device having at least two parts, including an internal part and an external part, each of the internal part and the external part consisting essentially of a metal that biodegrades within a living being in a period of time that permits biological repair of the blood vessel wall in and around the blood vessel aperture;

extending the internal part at least partially through the blood vessel wall aperture and into the lumen to at least partially block the blood vessel wall aperture; and moving the external part relative and the internal part relative to each other by tensioning a tensioning member between the internal part within the blood vessel lumen and the external part outside of the blood vessel wall.

In another example embodiment, the invention includes selecting the metal to be magnesium.

In another example embodiment, the invention includes selecting the magnesium to have a purity in a range from about 90.0 percent to about 99.99 percent.

In another example embodiment, the invention includes selecting at the magnesium to have a purity of about 99.80 percent.

In another example embodiment, the invention includes selecting at least one of the internal part and the external; part to have a surface topography that is altered by particulate blasting whereby biodegradation of at least part the closure device is facilitated.

In another example embodiment, the invention includes selecting at least one of the internal part and the external part to have a surface topography that is altered by particulate blasting with a metallic oxide wherein the metal in the metallic oxide is a different metal that the metal from which the parts are formed whereby biodegradation of at least part the closure device is facilitated.

In another example embodiment, the invention includes selecting the metal to be magnesium alloyed with another metal.

In another example embodiment, the invention includes selecting the other metal to comprise iron.

In another example embodiment, the invention includes selecting the other metal to comprise manganese.

DETAILED DESCRIPTION

Figure 1:
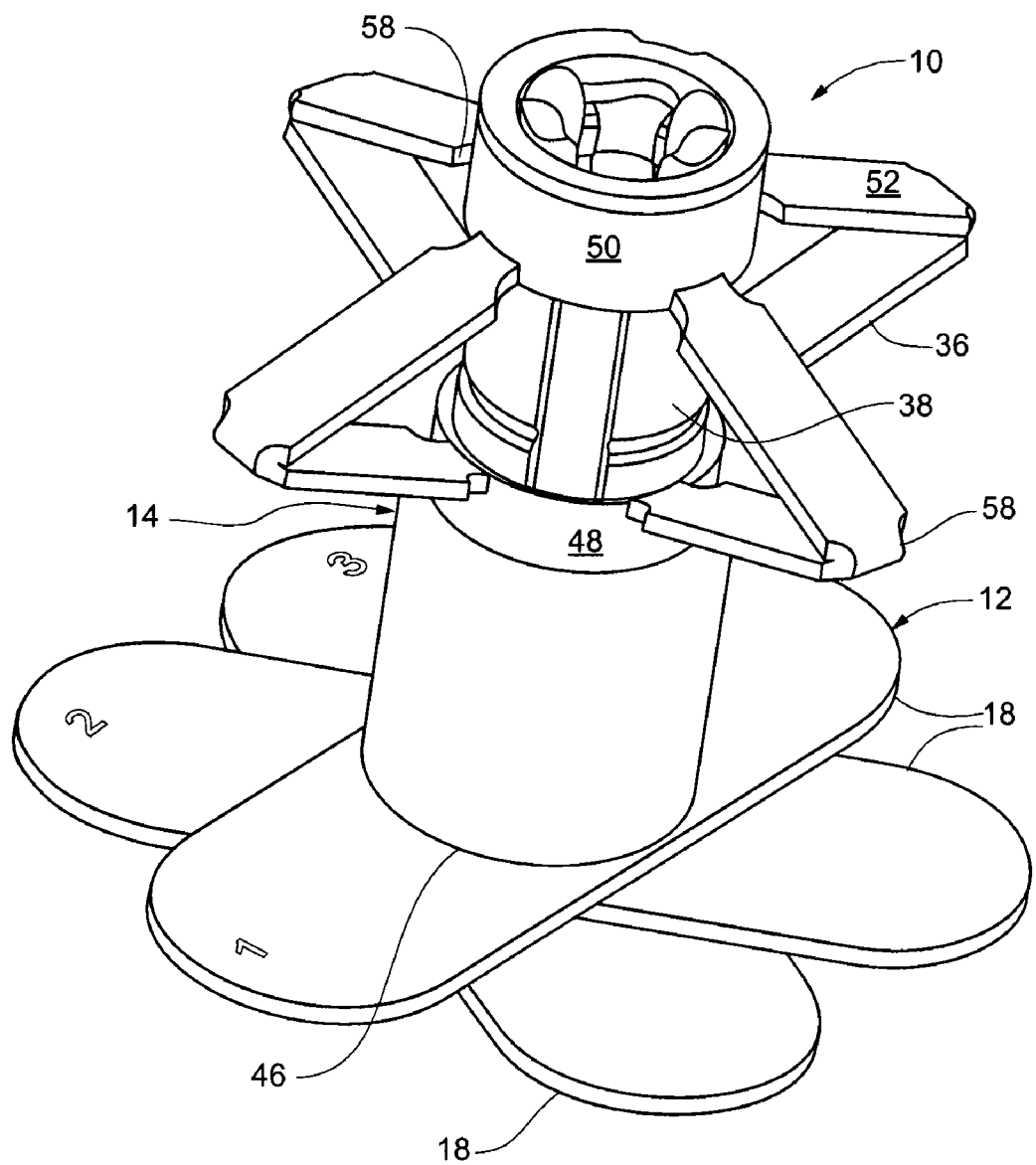
FIG. 1 is a perspective view of a closure device in accordance with the present invention.

Absorbable metal closure device 10 of an example embodiment of the invention as depicted in FIGS. 1-16 generally includes internal member 12, external member 14 and filament 16.

Internal member 12, in one example embodiment, includes two or more petals 18. Referring particularly to FIGS. 3-8, petals 18 are each pierced centrally by at least two apertures 20. The positioning of apertures 20, in these example embodiments, is related to the number of petals and determines the positional relationship of the petals 18 as will be discussed later.

Figure 8:
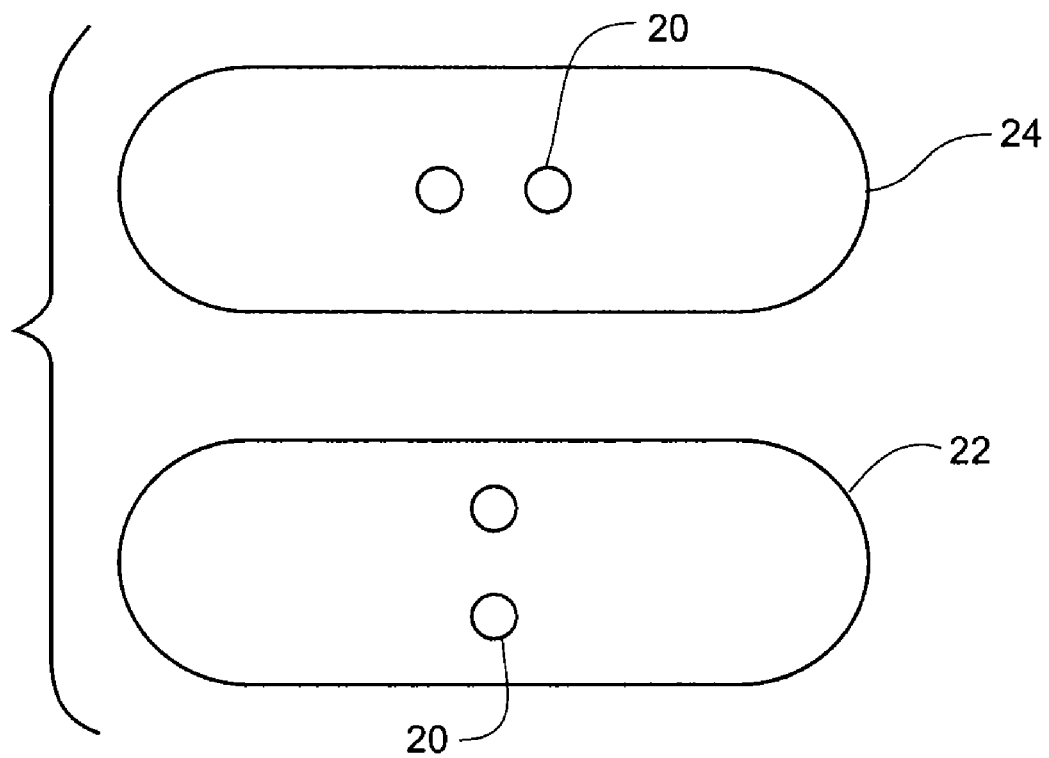
FIG. 8 is a plan view of two petals in accordance with an embodiment of the invention.
Figure 9:
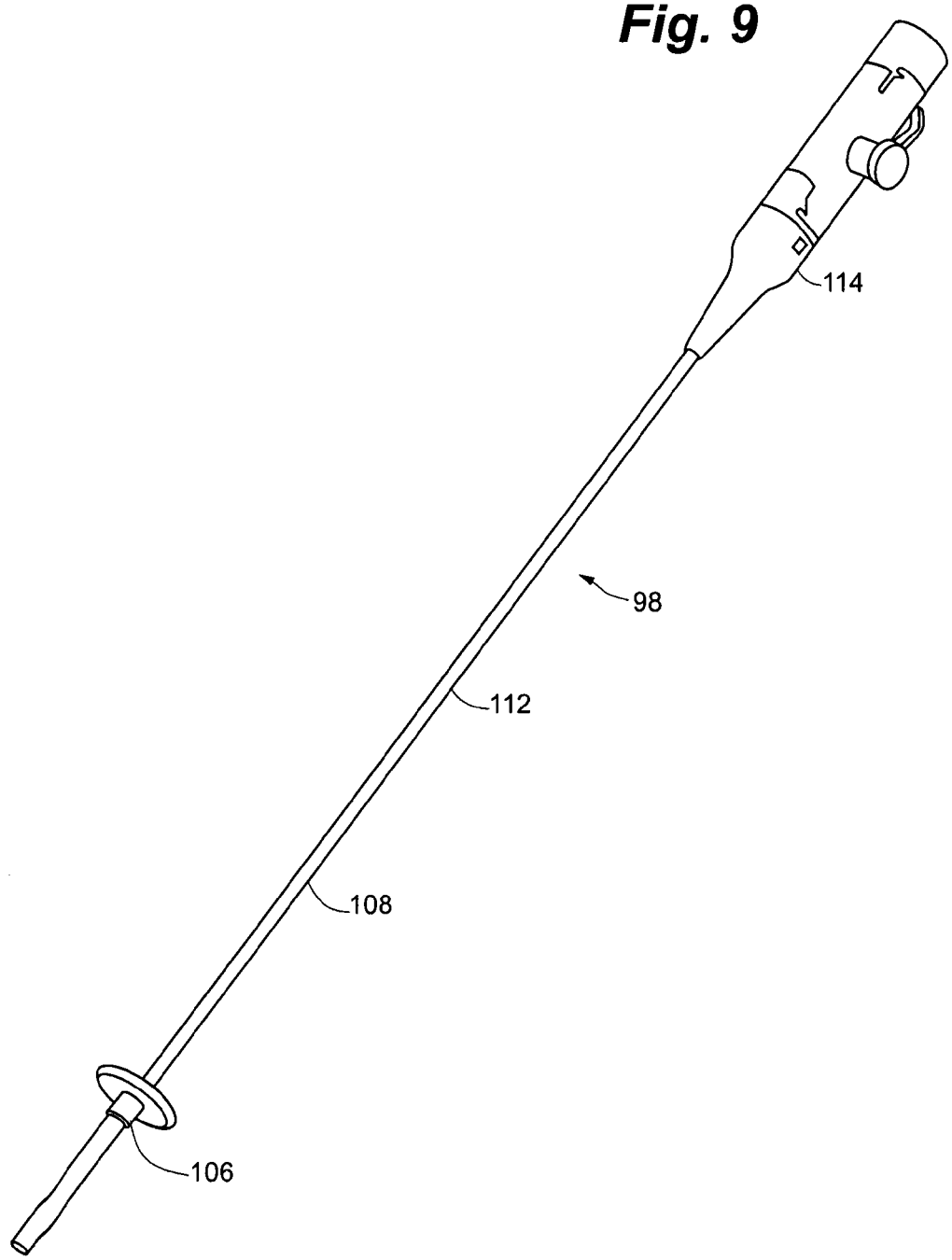
FIG. 9 is a perspective view of an insertion assembly in accordance with the invention.

In an example embodiment depicted in FIG. 8, including two petals 18, petals 18 include zero degree petal 22 and ninety degree petal 24. As can be seen zero degree petal 22 includes two apertures 20 aligned at approximately zero degrees to a short axis 32. Ninety degree petal 24 includes two apertures 20 aligned at approximately ninety degrees to short axis 32. It is not necessary to practice the invention that the specific angles along which the apertures are aligned given in these examples be used. It is only necessary that the variation between the angles of two related petals 18 be approximately equal to the desired relative rotational difference in position when deployed.

In an example embodiment including three petals 18, petals 18 include zero degree petal 26, sixty degree petal 28 and one hundred twenty degree petal 30. Zero degree petal 26 includes two apertures aligned at approximately zero degrees to short axis 32. Sixty degree petal 28 includes two apertures aligned at approximately sixty degrees to short axis 32. One hundred twenty degree petal 30 includes two apertures aligned at approximately one hundred twenty degrees to short axis 32.

In an example embodiment, filament 16 passes through apertures 20 of each petal. Filament 16 has sufficient flexibility so that when filament 16 is slack, petals 18 can be aligned generally parallel to one another prior to insertion. Petals 18 are dimensioned so as to be able to be passed through a catheter and then through a puncture wound in a blood vessel when they are aligned in a parallel orientation.

External member 14 generally includes stem portion 34, expandable portion 36 and locking part 38.

Figure 2:
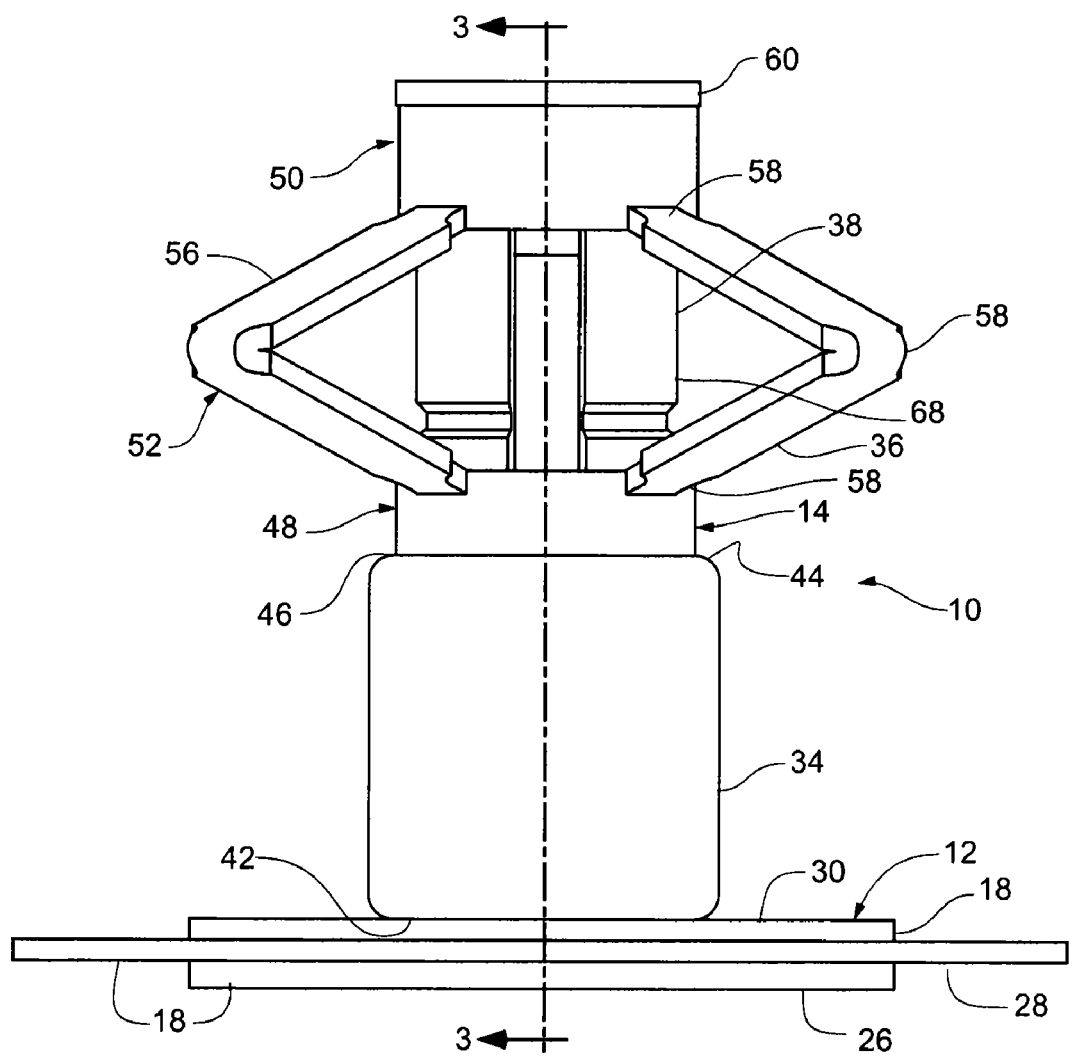
FIG. 2 is an elevational view of the closure device of FIG. 1.
Figure 3:
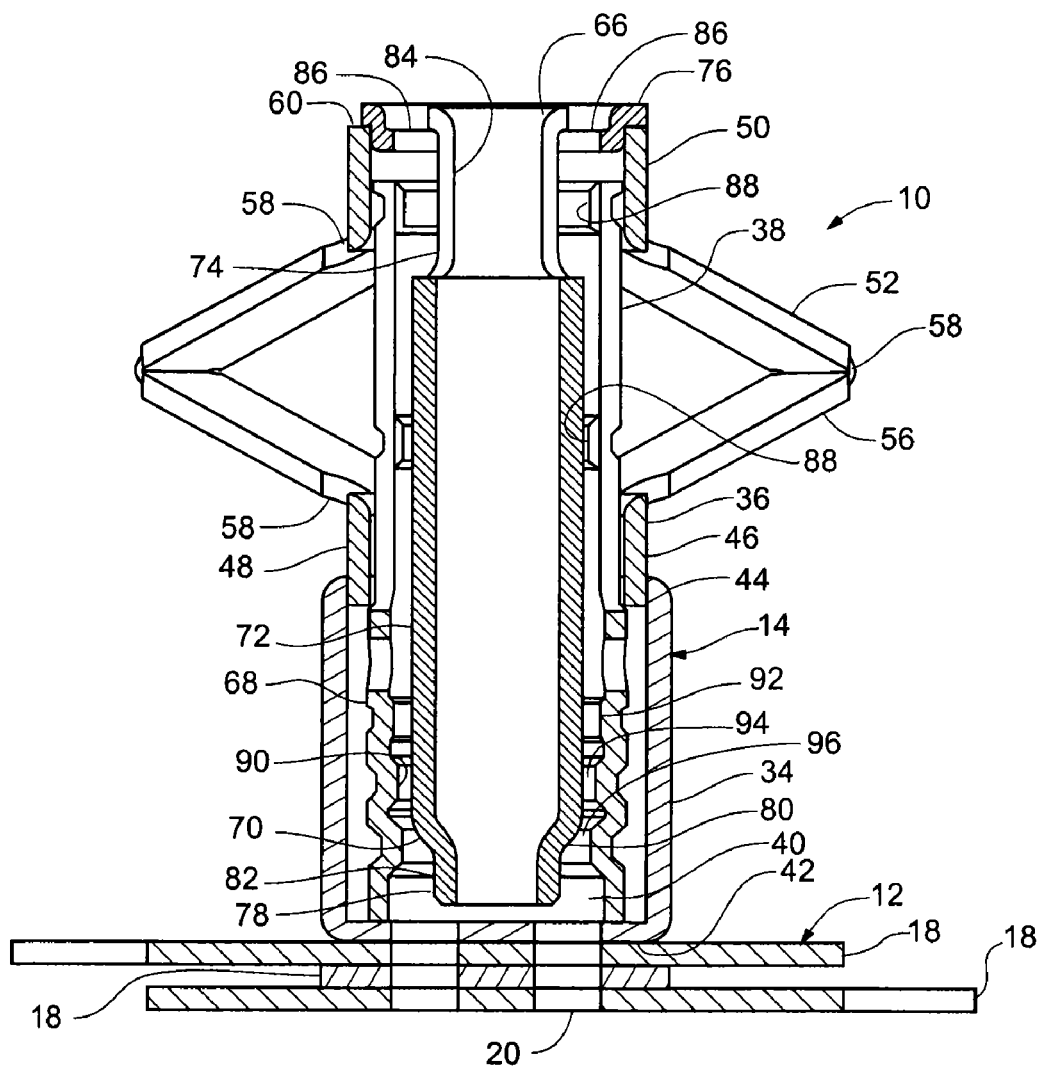
FIG. 3 is cross-sectional view of the closure device taken along section lines 3-3 of FIG. 2.

Referring to the example embodiment depicted in FIGS. 1-3, stem portion 34 is a generally cylindrical structure. In this example embodiment, stem portion 34 has a diameter approximately equal to the puncture wound to be sealed and which is also approximately equal to the width of petals 18. That is, stem portion 34 is sized to substantially fill the opening even if the placement of stem portion 34 into the opening alters the shape of the puncture or incision when it is inserted therein.

Stem portion 34 also defines at least one passage 40 therethrough sized to receive two strands of filament 16 either together or separately. Stem portion 34 is arranged along filament 16, along with petals 18 so that internal face 42 of stem portion 34 abuts to petals 18 when petals 18 are drawn against stem portion 34 by filament 16. External end 44 of stem portion 34 is arranged to abut expandable portion 36 when filament 16 is tensioned. In one example embodiment, external end 44 is permanently secured at distal end 46 of expandable portion 36. In one example embodiment, stem portion 34 may be permanently secured to expandable portion 36 such as by welding.

Figure 11:
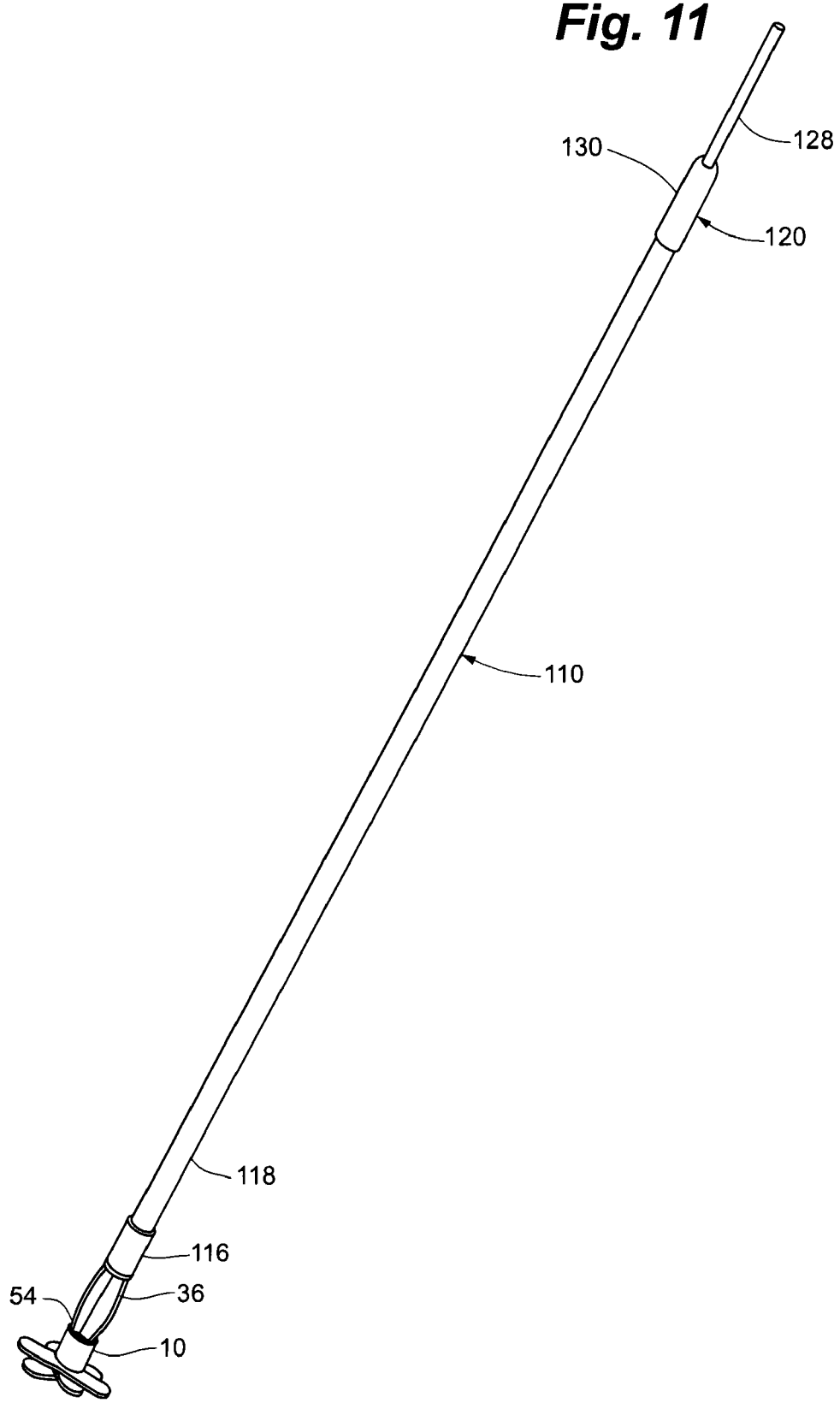
FIG. 11 is a perspective view of a closure device in the unexpanded state along with a deployment tube in accordance with the invention.
Figure 12:
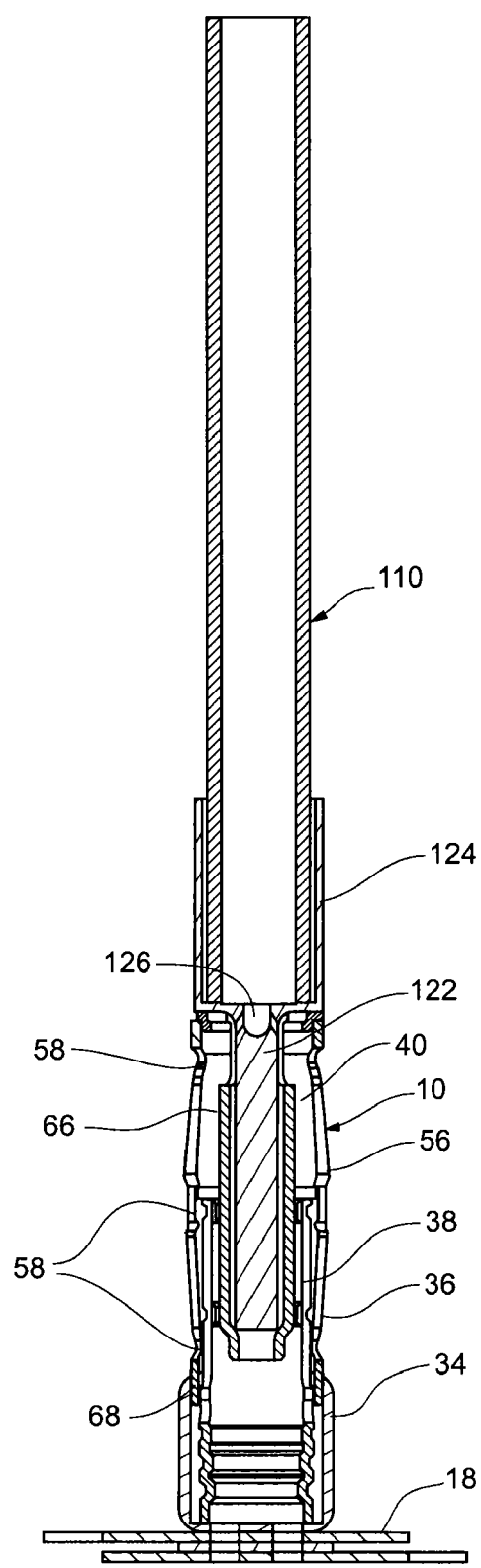
FIG. 12 is a sectional view of a closure device and the deployment tube in accordance with the invention.
Figure 13:
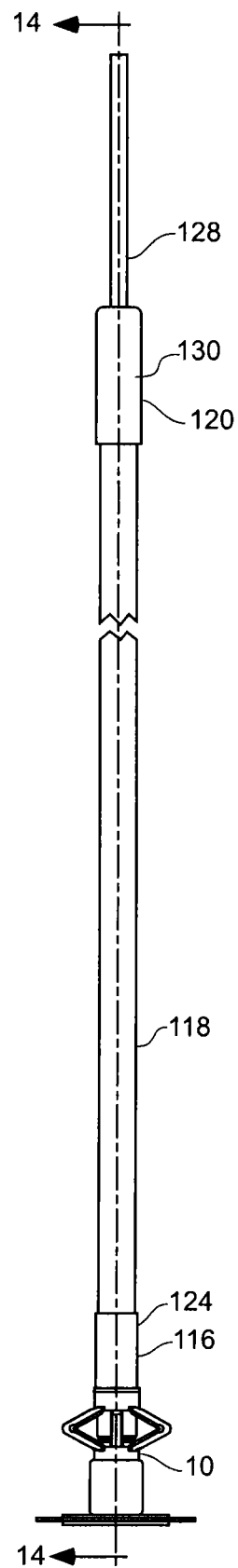
FIG. 13 is an elevational view of a closure device in the expanded state and a deployment tube in accordance with the invention.

Referring particularly to FIGS. 1-3 and 11-14, expandable portion 36 generally includes distal portion 48, proximal portion 50 and expansion portion 52. In one example embodiment, expandable portion 36 may take the form of any elongate hollow cylinder as can be seen in FIGS. 11 and 12. In this example, distal portion 48 and proximal portion 50 each include a complete portion of the cylinder, which is interrupted by expansion portion 52.

Expansion portion 52, in this embodiment, is formed by creating two or more slits 54 lengthwise in expandable portion 36. Between slits 54 remain expansion members 56.

Expansion members 56 may be bowed slightly outward centrally, as seen in FIG. 12, to facilitate expansion when distal portion 48 and proximal portion 50 move toward one another. Example embodiments of the invention may include two or more expansion members 56 which are shiftable from an unexpanded orientation to an expanded orientation. Example embodiments include four or six expansion members 56. Shifting of expansion members 56 from an unexpanded orientation to an expanded orientation may be accomplished by deformation of expansion members 56. In another embodiment of the invention, expansion members 56 may be reversibly shiftable. Expansion members 56 may also be created in an expansion portion 52, for example, by forming slits 54 in a spiral fashion rather than lengthwise relative to expandable portion 36.

In one example embodiment, as depicted in FIGS. 1-3, 11 and 12 expansion members 56 may include reduced cross-sectional areas 58 located at each end of expansion members 56 and at a central location of expansion members 56 to facilitate deformation of expansion members 56 in a desired way.

Figure 17:
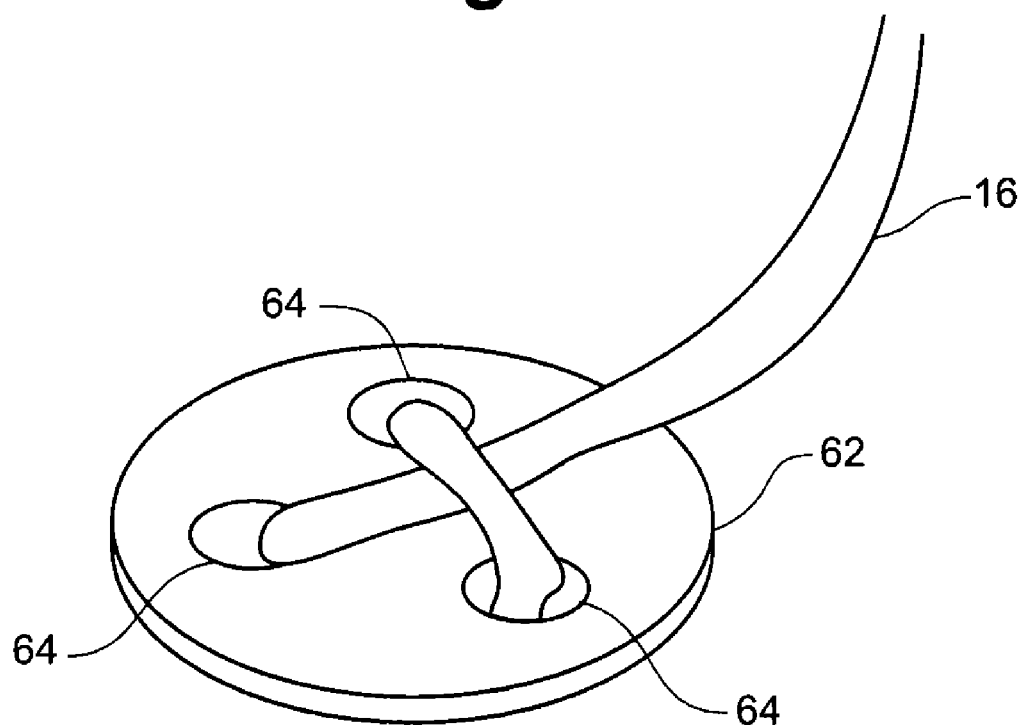
FIG. 17 is a perspective view of an aperture plate and filament in accordance with an embodiment of the invention.
Figure 18:
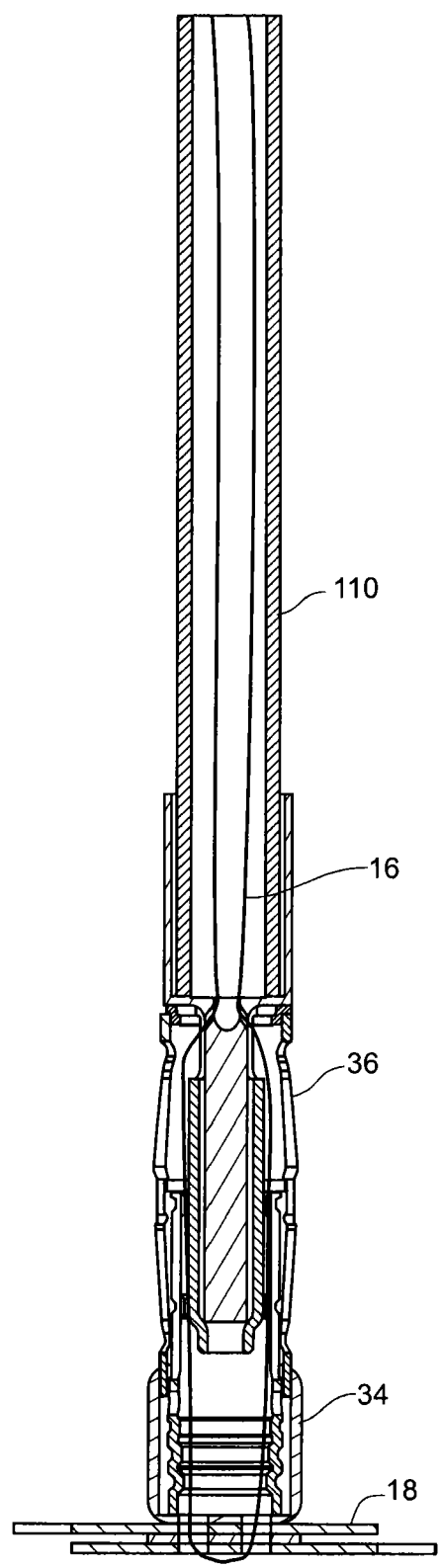
FIG. 18 is a sectional view of a closure device and the deployment tube as in FIG. 12 including a schematic depiction of a filament routing in accordance with an embodiment of the invention.
Figure 19:
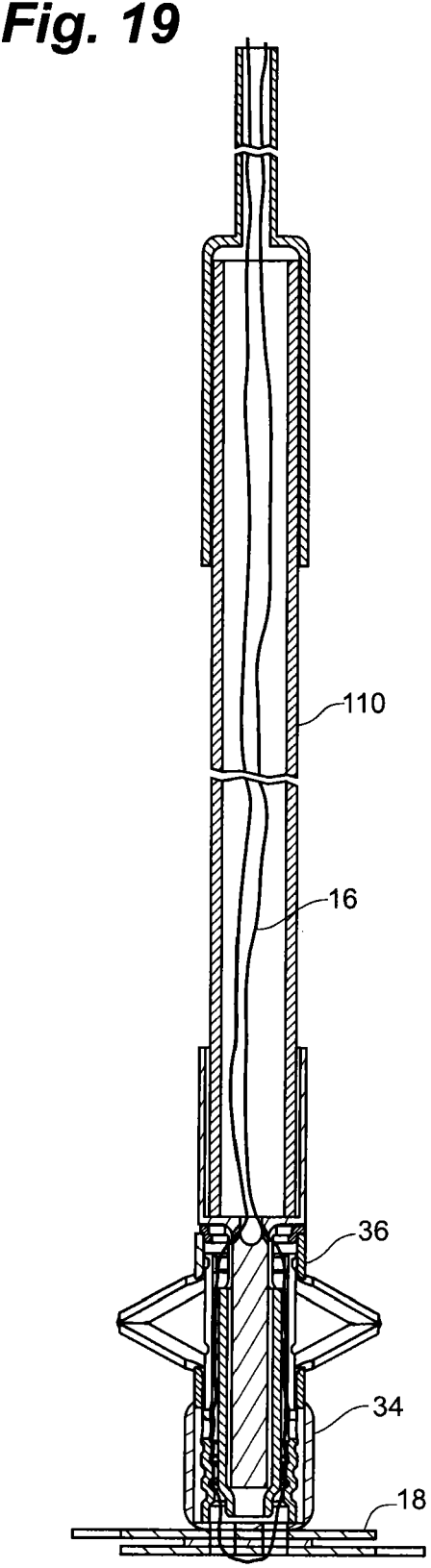
FIG. 19 is a sectional view as in FIG. 14 including a schematic depiction of a filament routing in accordance with an embodiment of the invention.

In another example embodiment of the invention, proximal end 60 of expandable portion 36 may include an open ended cylinder. In another example embodiment, proximal end 60 may be closed by aperture plate 62, depicted in FIG. 17. Aperture plate 62 may include two or more apertures 64 through which filament 16 may pass. In one example embodiment, aperture plate 62 includes three apertures 64 so that two strands of filament 16 may be passed in a proximal direction through a first aperture 64, then in a distal direction through a second aperture 64, then in a proximal direction again outward through the third aperture 64 and passed under strands of filament 16 where they pass between first aperture 64 and second aperture 64 to act as locking part 38.

Referring particularly to FIGS. 1-3, 12, 18, and 19, in another example embodiment, locking part 38 includes wedge 66 and wedge receiver 68. In this example embodiment, filament 16 is passed between wedge 66 and wedge receiver 68. Wedge 66 is shiftable relative to wedge receiver 68 so as to allow generally free movement of filament 16 when wedge 66 is spaced from wedge receiver 68 or so as secure filament 16 in at least one direction against movement by friction and compression when wedge 66 is urged toward wedge receiver 68.

In another example embodiment, locking part 38 includes cam (not shown.) Cam (not shown) is configured to pinch filament 16 against a surface in order to securely lock filament 16 from movement in at least one direction by friction and compression.

Referring to FIGS. 1-3 and 12-14, in this example embodiment, wedge receiver 68 is located within stem portion 34 and expandable portion 36, generally coaxially with stem portion 34 and expandable portion 36. Wedge 66 is then located generally coaxially within wedge receiver 68. Wedge 66 generally includes tapered distal portion 70, intermediate shaft 72, tail portion 74 and proximal cap 76. Tapered distal portion 70 generally includes nose portion 78 and sloped portion 80. Nose portion 78 may have generally parallel sides 82 followed by sloped portion 80. In this example embodiment, intermediate shaft 72 is a generally cylindrical hollow structure. Intermediate shaft 72 merges into tail portion 74, which is smaller in diameter than intermediate shaft 72 and pierced by suture apertures 84. Proximal cap 76 is joined to tail portion 74 and sized to abut proximal end 60 of expandable portion 36. Proximal cap 76 is also pierced by suture apertures 86.

In the depicted example embodiment, wedge receiver 68 defines, on the interior surface thereof, alignment ribs 88. Alignment ribs 88 are sized to permit the free but closely aligned passage of wedge 66 within wedge receiver 68. Wedge receiver 68 also defines on an inside surface thereof retention ribs 90. Proximal retention rib 92, intermediate retention rib 94 and distal retention 96 are present.

In this example embodiment, proximal retention rib 92 defines a circular opening of a first size, intermediate retention rib 94 defines a smaller opening than proximal retention rib 92 and distal retention rib 96 defines a yet smaller opening than intermediate retention rib 94. Thus, the clearance between wedge 66, when it is advanced into wedge receiver 68, is reduced to a dimension appropriate to secure filament 16 between wedge 66 and wedge receiver 68 by friction and compression. When wedge 66 is not advanced into wedge receiver 68, there is clearance between wedge 66 and wedge receiver 68 in the area of retention ribs 90 for the relatively free movement of filament 16 therebetween.

Referring particularly to FIGS. 3 and 12, proximal cap 76 is secured to tail portion 74 of wedge 66 and to proximal end 60 of expansion portion 52 so that wedge 66 and proximal end 60 of expansion portion 52 advance together as expansion portion 52 shifts from an unexpanded status to a expanded status.

Figure 10:
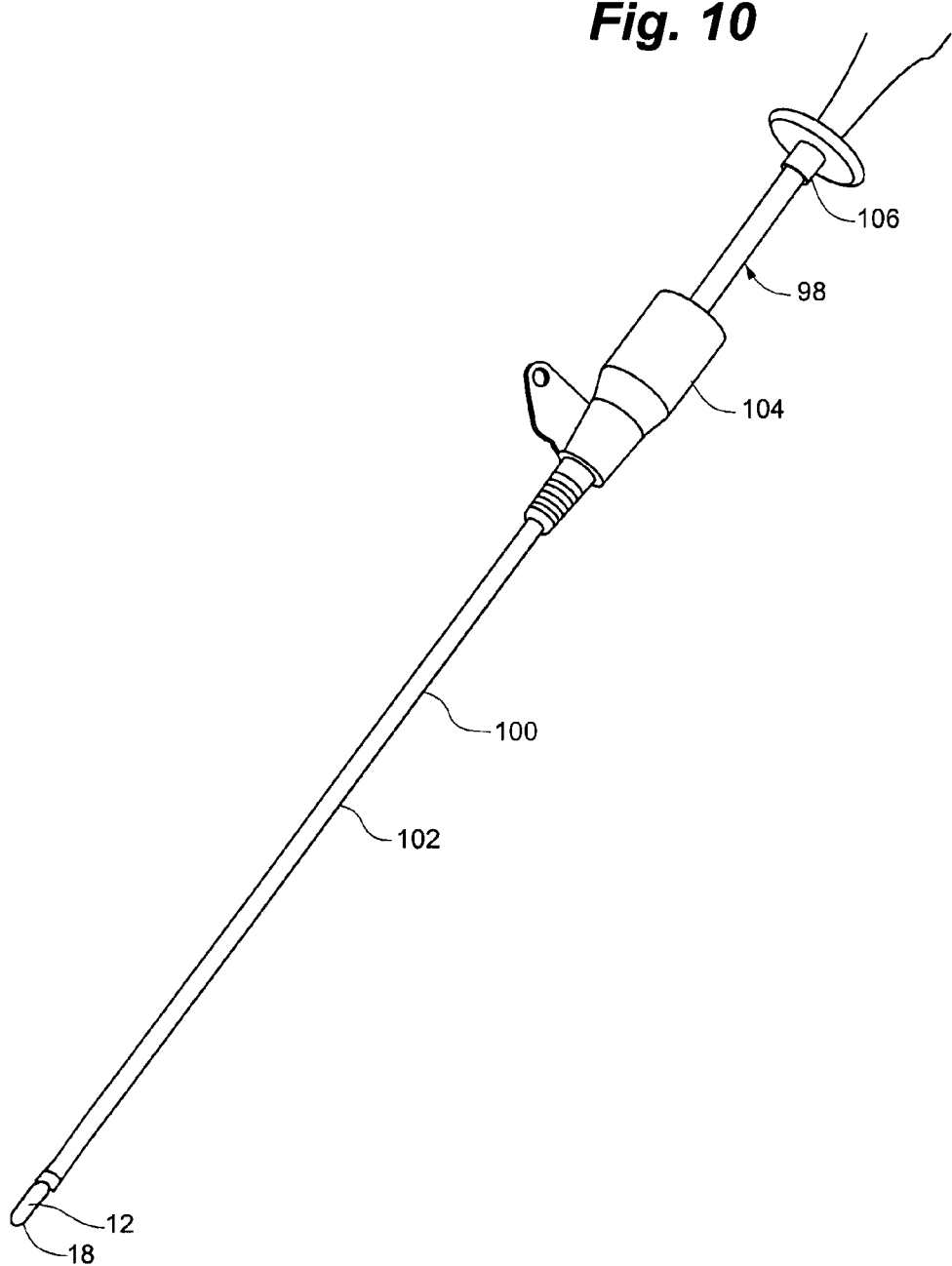
FIG. 10 is a perspective view of an insertion assembly inserted in a sheath in accordance with the present invention with petals partially exposed beyond the sheath.

Referring to FIGS. 9-16, closure device 10 of the present invention may be utilized with the assistance of insertion assembly 98 and through preplaced sheath 100. Sheath 100, as depicted in FIG. 10, is a generally conventional introducer sheath assembly having a tubular portion 102 and a resilient valve 104.

Insertion assembly 98 generally includes bypass tube 106, delivery tube 108 and deployment tube 110. Bypass tube 106 is located exteriormost and allows the passage of the remainder of insertion assembly 98 through resilient valve 104 of sheath 100.

Delivery tube 108, in the depicted example embodiment, includes tubular portion 112 and handle 114. In one example embodiment of the invention, handle 114 may include push button release 115 adapted to secure filament 16 therein. Tubular portion 112 is sized to receive deployment tube 110 therein as well as closure device 10 with expansion portion in the unexpanded state and petals 18 aligned generally parallel to one another and parallel to tubular portion 112 of delivery tube 108.

Deployment tube 110 is sized to fit within delivery tube 108 and adapted to engage tail portion 74 of wedge 66 as well as proximal portion 50 of expandable portion 36.

Referring to FIGS. 11-14, deployment tube 110 generally includes distal end 116, hollow shaft 118 and proximal end 120.

Distal end 116 generally includes probe 122 and collar 124. Probe 122 extends outwardly away from collar 124 coaxial with hollow shaft 118 in this example embodiment. Probe 122 is dimensioned to fit within wedge 68. Collar 124 is dimensioned to receive hollow shaft 118 therein and pierced by filament apertures 126 proximate the base of probe 122. Filament apertures 126 are sized to pass filament 16 therethrough and are located near the junction between probe 122 and collar 124. Collar 124 is secured to collar shaft 118.

Proximal end 120 generally includes extension tube 128 and proximal collar 130. Extension tube 128 is hollow and sized to receive filament 16 therein in a snuggly fitting relationship. Proximal collar 130 is sized to be secured to hollow shaft 118 of deployment tube 110. As such, there is a continuous passage through extension tube 128, hollow shaft 118 and filament apertures 126 such that filament 116 may pass entirely through deployment tube 110.

Figure 20A:
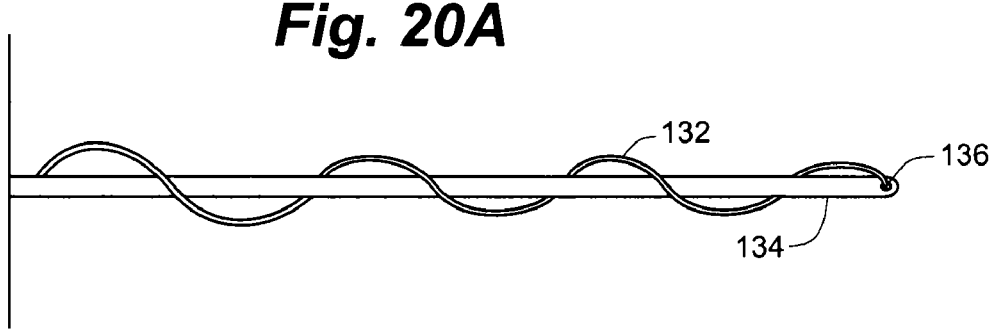
FIG. 20A-C is a sequential plan view of an alternative embodiment of an external member in accordance with the invention.
Figure 20B:
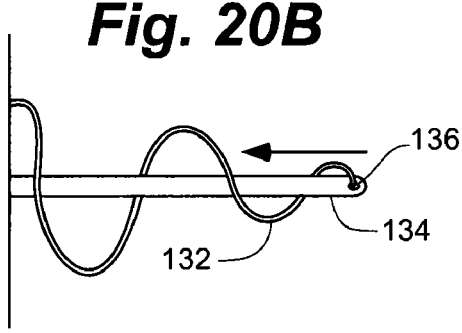
Figure 20C:
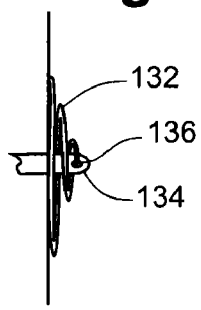

Referring to FIG. 20A-C, in another example embodiment, external member 14 includes coiled member 132 and linear member 134. As can be seen in FIG. 20, linear member 134 is joined to coiled member 132 at eyelet 136. Coiled member 132, as depicted in FIG. 20A, is extended along linear member 134 for insertion. Coiled member 132 is expandable by withdrawal of linear member 134 as depicted in FIGS. 20B and 20C. FIG. 20C depicts coiled member 132 in a fully expanded state. Coiled member 132 is joined to linear member 134 so that rotation of linear member 134 twists coiled member 132 to adjust the diameter or extended state of coiled member 132. Twisting in one direction increases the diameter of coiled member 132. Twisting in the opposed direction decreases the diameter of coiled member 132.

Figure 21A:
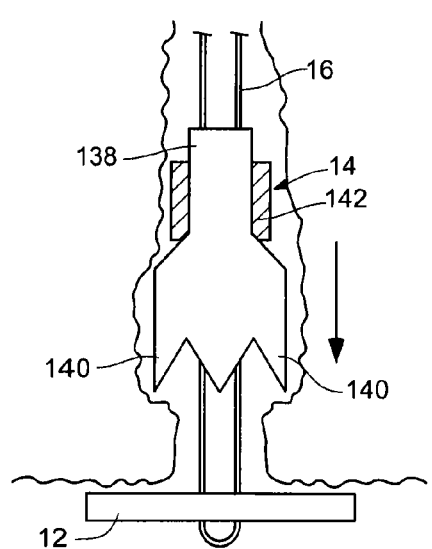
FIG. 21A-C is a schematic sequential plan view of another alternative embodiment of an external member in accordance with the invention.
Figure 21B:
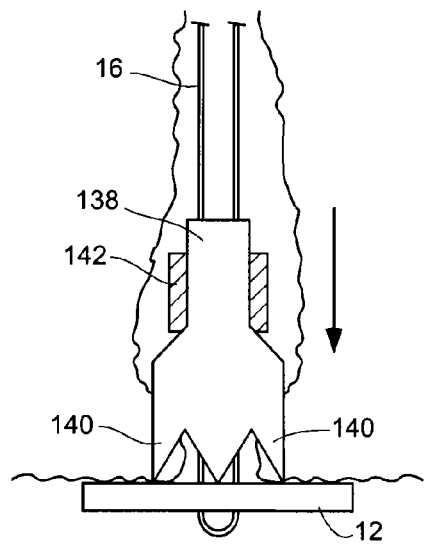
Figure 21C:
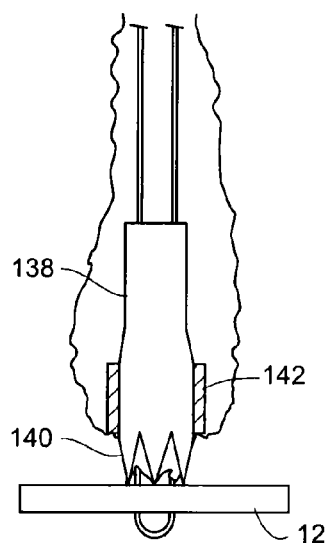

Referring to FIGS. 21A-C, another example embodiment of external member 14 is depicted in sequence. In this example embodiment, external member 14 generally includes body 138, fingers 140 and deformation sleeve 142. Filament 16 passes through body 138 and secures this embodiment of external member 14 to internal member 12. Deformation sleeve 142 is slidably disposed upon body 138. Deformation sleeve 142 is sized to deform FIG. 140 from an open state as depicted in FIGS. 21A and 21B to a closed state depicted in FIG. 21C as deformation sleeve 142 is moved distally along body 138. Deformation sleeve 142 may be advanced by use of a tubular push structure (not shown) while tension is held on filament 16. Fingers 140 are structured to grip tissue that may be located at the distal end of this embodiment of external member 14 when deformation sleeve 142 is advanced over fingers 140.

Figure 22:
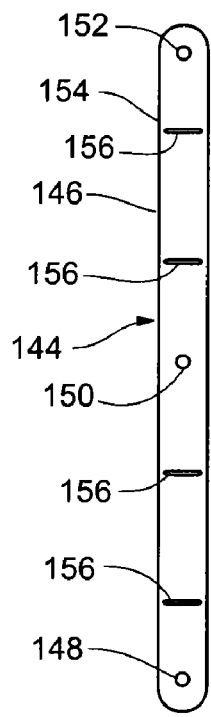
FIG. 22 is a plan view of another alternative embodiment of an external member in an elongated state in accordance with the invention.
Figure 23:
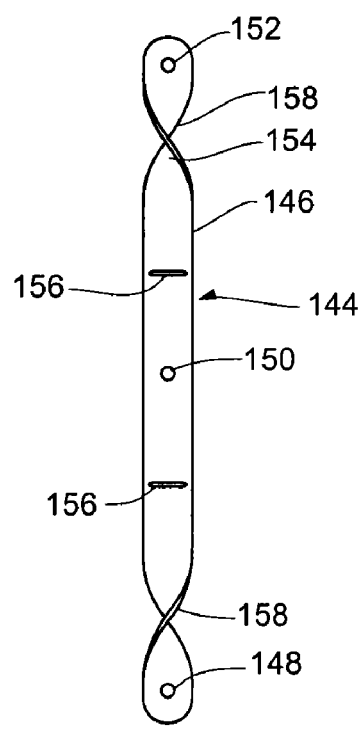
FIG. 23 is a plan view of another alternative embodiment of an external member in an elongated state in accordance with the invention.

Referring to FIGS. 22 and 23, two more alternative example embodiments of internal member 12 are depicted. The embodiments depicted in FIGS. 22 and 23 operate in a similar fashion and will be described together. Metal linear deformable member 144 includes elongate body 146. Elongate body 146 is pierced by distal aperture 148, central aperture 150 and proximal aperture 152. Elongate body 146 also presents bend facilitators 154.

Referring particularly to FIG. 22, example bend facilitators 154 may include crimped or thinned sections 156. Crimped or thinned sections 156 may include areas of reduce cross sectional area. Referring particularly to FIG. 23, in another example embodiment bend facilitators 154 include twists joints 158. Bend facilitators 154 help control the deformation of elongate body 146. Filament 16 may be passed through distal aperture 148, central aperture 150 and proximal aperture 152. Filament 16 also helps control the deformation of elongate body 146.

Figure 24:
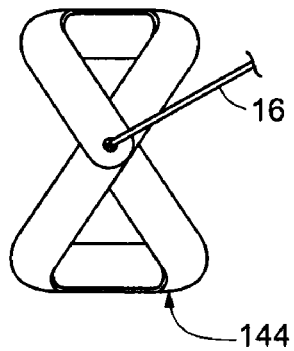
FIG. 24 is a plan view of the alternative embodiment of FIG. 22 or 23 in a deformed expanded state.

Referring now to FIG. 24, metal linear deformable member 144 is depicted in a deformed and expanded state after force has been applied along its long axis while holding tension on filament 16 to draw distal aperture 148 into contract with central aperture 150 and central aperture 150 into contact with proximal aperture 152. Bend facilitators 154 permit elongate body 146 to be bent to assume, in this example embodiment, a bow tie configuration. Thus, metal linear deformable member 144 expands to secure its location and filament 16 in a tissue tract or in a location external to a blood vessel wall.

Figure 25:
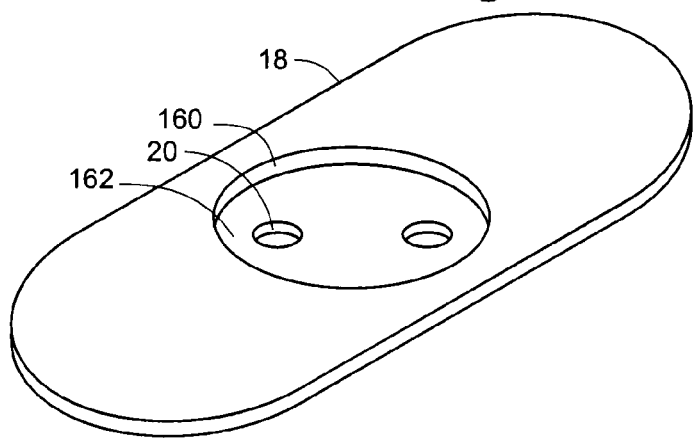
FIG. 25 is a perspective view of an alternative embodiment of a petal in accordance with the invention.
Figure 26:
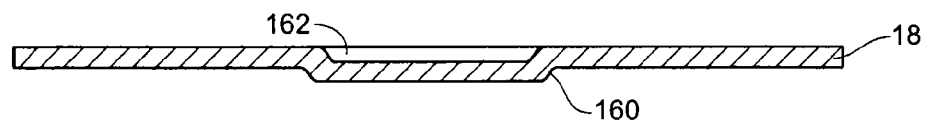
FIG. 26 is a cross sectional view of the petal depicted in FIG. 25.
Figure 27:
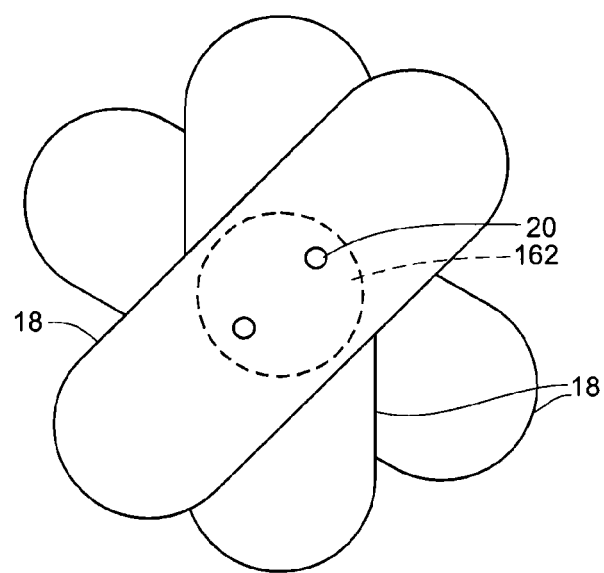
FIG. 27 is a plan view of the petal depicted in FIGS. 25 and 26 along with other petals.

Referring to FIGS. 25, 26 and 27, an alternative embodiment of petals 18 is depicted. Referring to FIG. 25, in this example, petal 18 includes indentation 160 defining pocket 162. Pocket 162 may be centrally located and in the depicted embodiment surrounds apertures 20. Referring particularly to FIG. 27, in this embodiment, pocket 162 is located to be covered by adjacent petals 18 in the deployed orientation. Pocket 162 may contain a buffer as described elsewhere in this application.

Figure 28:
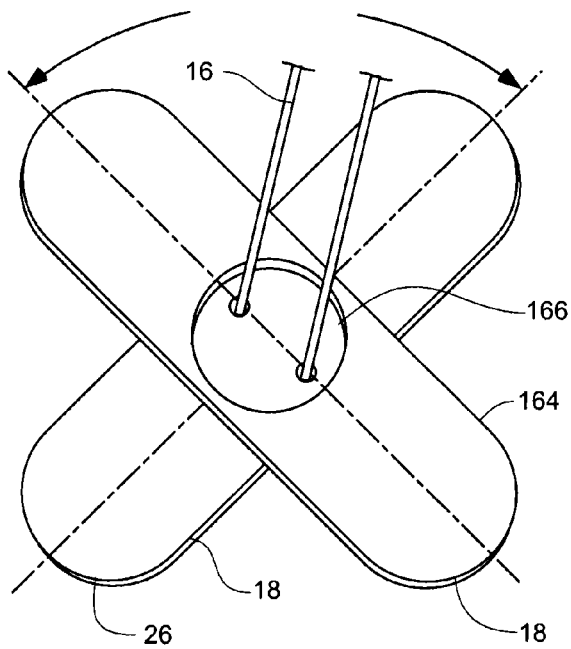
FIG. 28 is a perspective view of two petals in accordance in an alternative embodiment of the invention.
Figure 29:
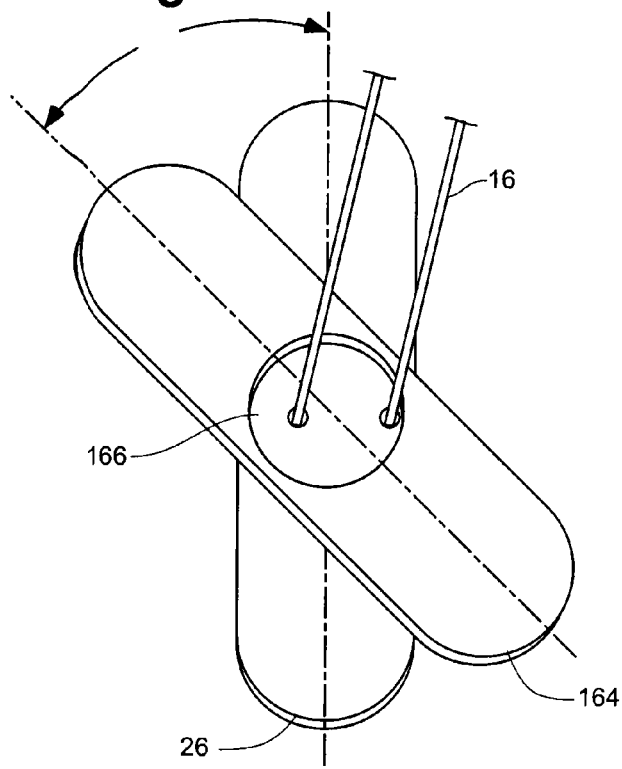
FIG. 29 is a perspective view of two petals as depicted in FIG. 28 in another angular orientation.

Referring to FIGS. 28 and 29, yet another embodiment of petals 18 is depicted. In this embodiment, zero degree petal 26 is depicted adjacent to large aperture petal 164. FIG. 28 depicts zero degree petal 26 oriented displaced approximately ninety degrees from large aperture petal 164. FIG. 29 depicts zero degree petal 26 oriented at an acute angle to large aperture petal 164. Large aperture petal 164 defines large aperture 166 therethrough. Large aperture 166 is of sufficient size to allow the passage of filament 16 passing through apertures 20 of zero degree petal 26 and to permit free rotation of larger aperture petal 164 about filament 16 relative to zero degree petal 26. As such, when unrestricted, large aperture petal 164, of which there may be more than one, can assume a random orientation relative to zero degree petal 26.

Figure 31:
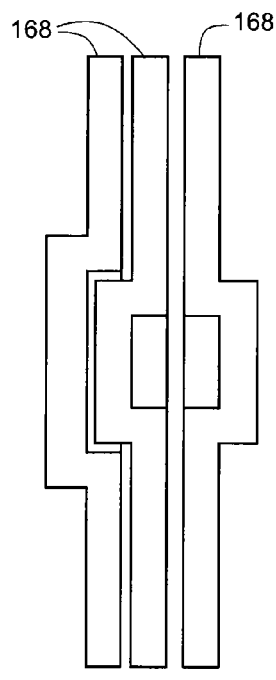
FIG. 31 is a cross sectional view of three petals in a parallel orientation as depicted in FIG. 30.
Figure 30:
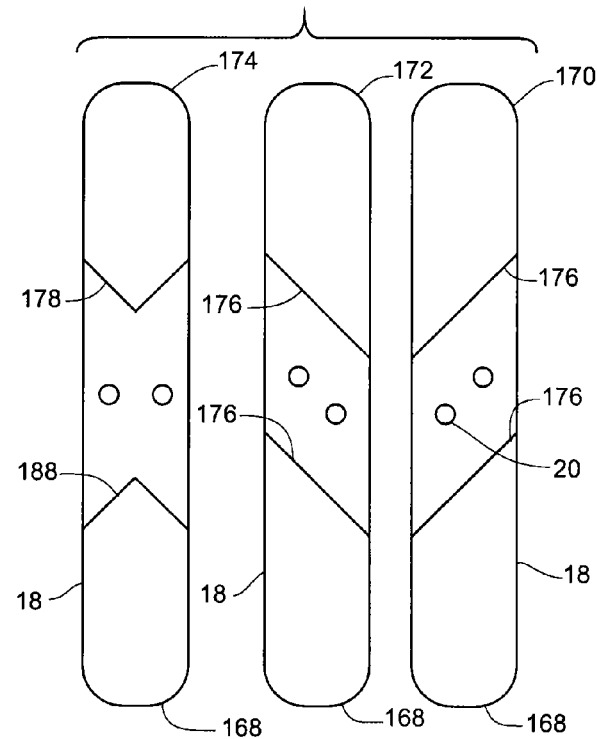
FIG. 30 is a plan view of three petals in accordance with another alternative embodiment in accordance with the invention.
Figure 32:
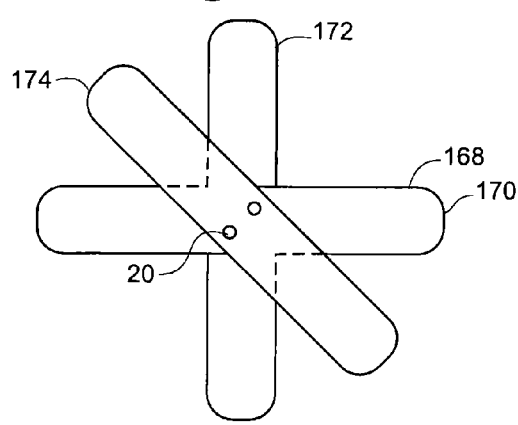
FIG. 32 is a plan view of the three petals as depicted in FIGS. 30 and 31 in a fanned out or deployed orientation.
Figure 33:
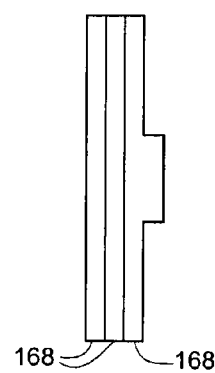
FIG. 33 is a cross sectional view take along section line 33-33 of FIG. 32.

Referring now to FIGS. 31-33, another embodiment of petals 18 is depicted. Referring particularly to FIG. 30, ridge petals 168 include first ridge petal 170, second ridge petal 172 and third ridge petal 174. First ridge petal 170 includes diagonal ridges 176. Second ridge petal 172 includes diagonal ridges 176 at a different angle than first ridge petal 170. Third ridge petal 174 includes V-ridges 178. Diagonal ridges 176 and V-ridges 178 are oriented to urge first ridge petal 170, second ridge petal 172 and third ridge petal 174 into an orientation as depicted in FIG. 32. Ridge petals 168 are depicted including two apertures 20 in each ridge petals 168. However, a single aperture 20 is sufficient for ridge petals 168.

Referring to FIG. 31, ridge petals 168 are depicted in cross section in a stacked parallel orientation. Referring to FIG. 33, ridge petals 168 are depicted in cross section in a fanned out or a deployed orientation.

The operation of closure device 10 will first be described in a general fashion. Thereafter, operation will be described in greater detail.

Prior to insertion into a tissue tract, closure device 10 is arranged in insertion assembly 98 such that filament 16 is doubled and free ends of filament 16 pass through apertures 20 in petals 18 then through stem portion 34 then through expandable portion 36, through locking part 38 and proximally out through delivery tube 72 leaving a substantial length of free ends of filament 16 available to remain outside of the body when insertion assembly 98 is inserted into a tissue tract. Closure device 10 is then located in a delivery tube 108 so that petals 18 are aligned substantially parallel lengthwise to one another and parallel to the long axis of delivery tube 108. Petals 18 are followed by stem portion 34 followed by expandable portion 36 including locking part 38, all of which are threaded onto filament 16.

Insertion assembly 98 holding closure device 10 is then passed through sheath 100 which remains in the tissue tract from the surgical procedure previously performed. Deployment tube 110 may be used to push closure device 10 forward through delivery tube 108 and through the puncture in the blood vessel wall and into the blood vessel lumen. The delivery tube 108, holding closure device 10, is advanced until its distal end is at least partially within the blood vessel which has an incision or a puncture wound in it. Closure device 10 is then advanced until at least petals 18 and stem portion 34 are within the lumen or beyond the incision.

After petals 18 are within the lumen of the blood vessel, filament 16 is tensioned from outside of the body of the treated individual. Tensioning filament 16 causes petals 18 to transition from a substantially parallel aligned orientation to a fanned out orientation such that petals 18 are now usually arranged at substantially equal geometric angular orientations. For example, an embodiment including three petals 18, petals 18 would be oriented at about sixty degree intervals. Closure device 10 is then withdrawn by tension on filament 16 until petals 18 are approximated against the interior blood vessel wall. Stem portion 34 then is located within the incision in the blood vessel wall and, in the case of a slit like incision, has caused the incision to attain a cylindrical configuration around stem portion 34.

Tension is then maintained on filament 16 and a pushing force is applied to delivery tube 72 to compress expansion portion 52 end to end while expanding expansion members 56 outwardly to the sides. As expansion members 56 deform they also move forward thus drawing petals 18 toward distal portion 48 of expandable portion 36. This action acts to compress the blood vessel wall, as well as intervening tissues between petals 18 and expandable portion 36.

Thus, the combination of petals 18, stem portion 34 and expandable portion 36 serves to seal the puncture blood vessel to prevent leakage of blood.

Once expandable portion 36 has achieved a longitudinally compressed and transversely expanded state, filament 16 is secured by locking part 38.

More specifically, in an example embodiment of closure device 10, in operation, closure device 10 is located within insertion assembly 98. Insertion assembly 98 is inserted into sheath 100 which generally remains in place after a vascular puncture procedure has been performed. Closure device 10 is located within delivery tube 108. Bypass tube 106 is located near the distal end of delivery tube 108. Bypass tube 106 is fitted into resilient valve 104 thus opening resilient valve 104 to protect against possible damage to closure device 10 and insertion assembly 98 as they pass through resilient valve 104.

Figure 4:
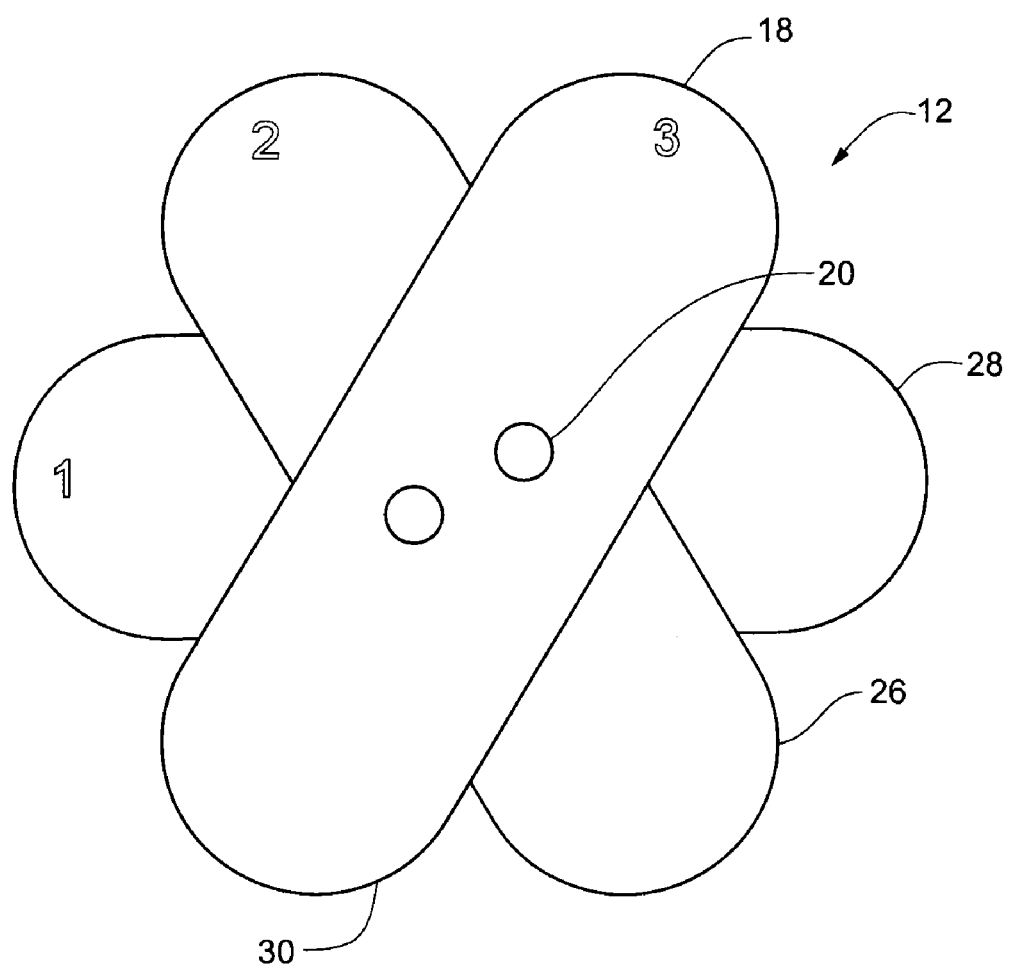
FIG. 4 is a plan view of 3 petals in accordance with an embodiment of the present invention.
Figure 5:
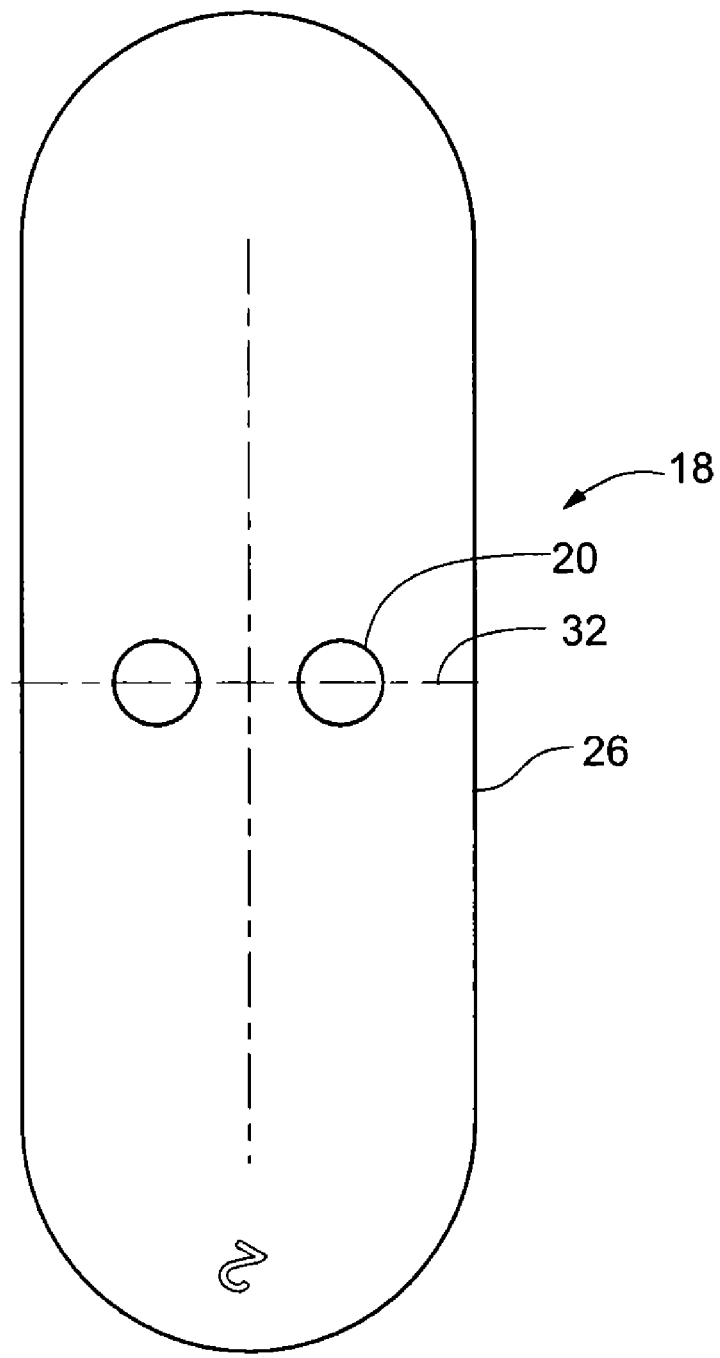
FIG. 5 is a plan view of a petal in accordance with the present invention.
Figure 6:
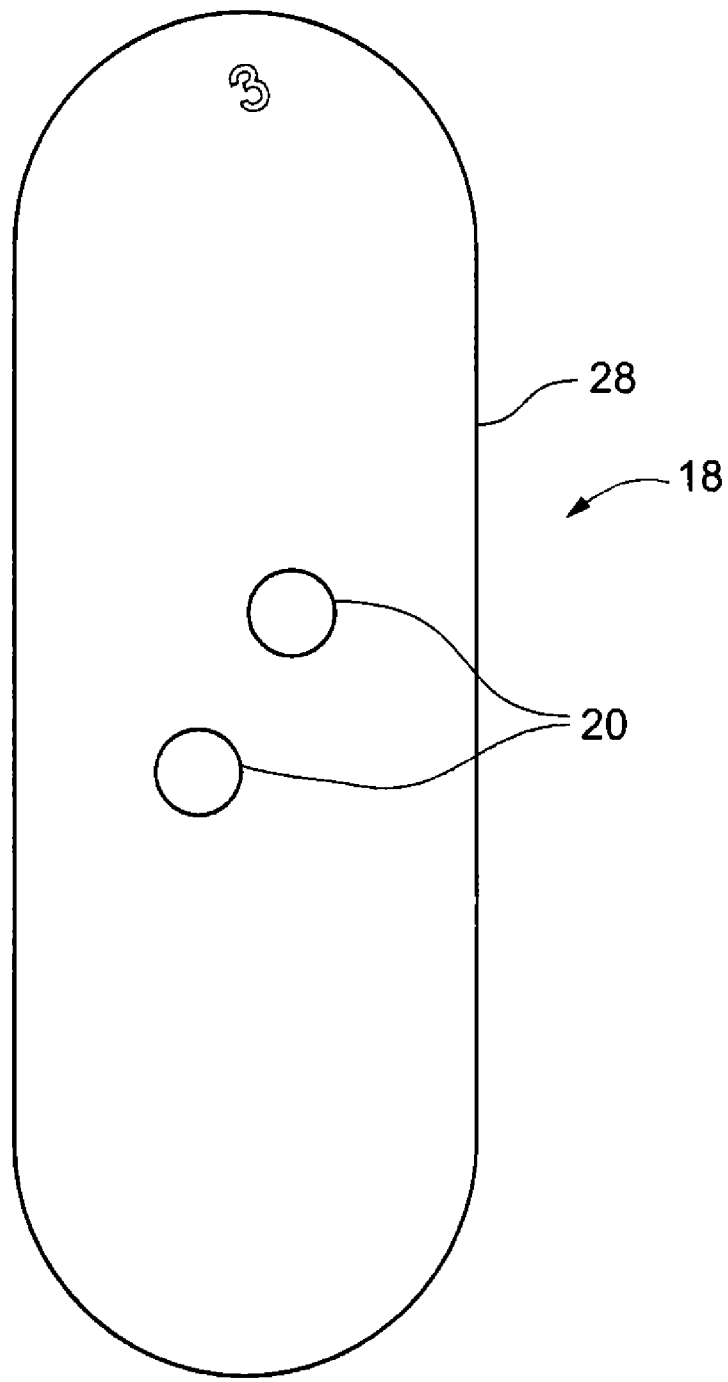
FIG. 6 is a plan view of another petal in accordance with the present invention.
Figure 7:
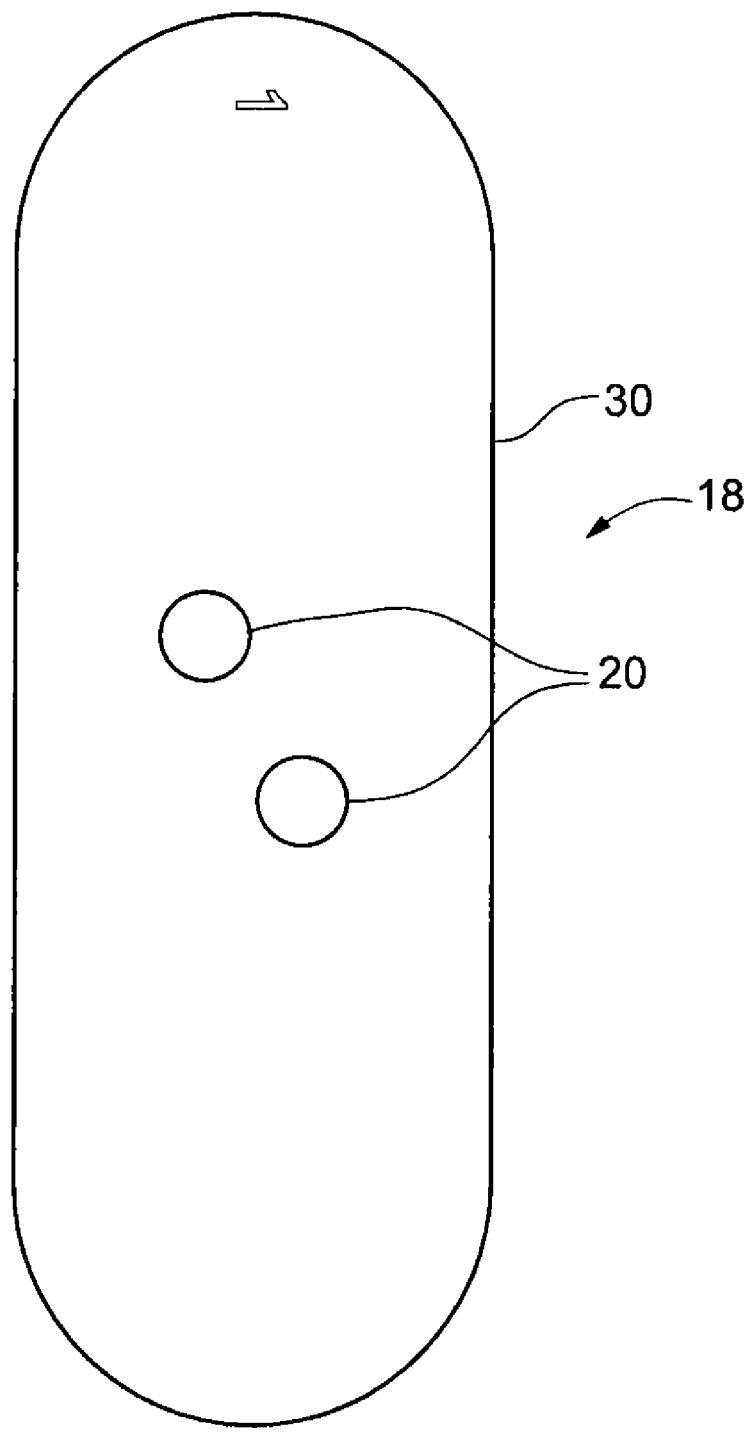
FIG. 7 is a plan view of yet another petal in accordance with the present invention.

Insertion assembly 98 is advanced through sheath 100 until internal member 12 including petals 18 passes into the lumen of an artery through an incision therein as depicted in FIG. 10. Deployment tube 110 is advanced through delivery tube 108 to advance closure device 10 until it is positioned to extend at least petals 18 and a portion of stem portion 44 out of delivery tube 108 into the artery lumen. Once released into the artery lumen, petals 18 tend to self-deploy once freed from delivery tube 108. This occurs because of the resiliency of filament 16 and because of the flow of blood within the lumen of the blood vessel. Petals 18 tend to generally align along filament 16 so that apertures 20 falls into line along filament 16 and petals 18 achieve an orientation relative to each other based on the location of apertures 20 in each petal 18. For example, zero degree petal 26, sixty degree petal 28 and one hundred twenty degree petal 30 with align at zero, sixty and one hundred twenty degrees relative to each other as depicted in FIGS. 1, 4 and 11.

Once petals 18 are fanned out and aligned, filament 16 is tensioned to pull petals 18 against artery wall. Push button release 115 on handle 114 is pressed to release filament 16 and bypass tube 106 and delivery tube 108 may be withdrawn from the tissue tract along with sheath 100.

At this point, deployment tube 110 and closure device 10 including stem portion 34, expandable portion 36 and locking part 38 remain within the tissue tract. Petals 18 are located within the lumen of the blood vessel proximate the blood vessel wall. Filament 16 passes through petals 18, stem portion 34, expandable portion 36, locking part 38 and deployment tube 110. Extension tube 128 is dimensioned to receive filament 16 closely therein.

Figure 15:
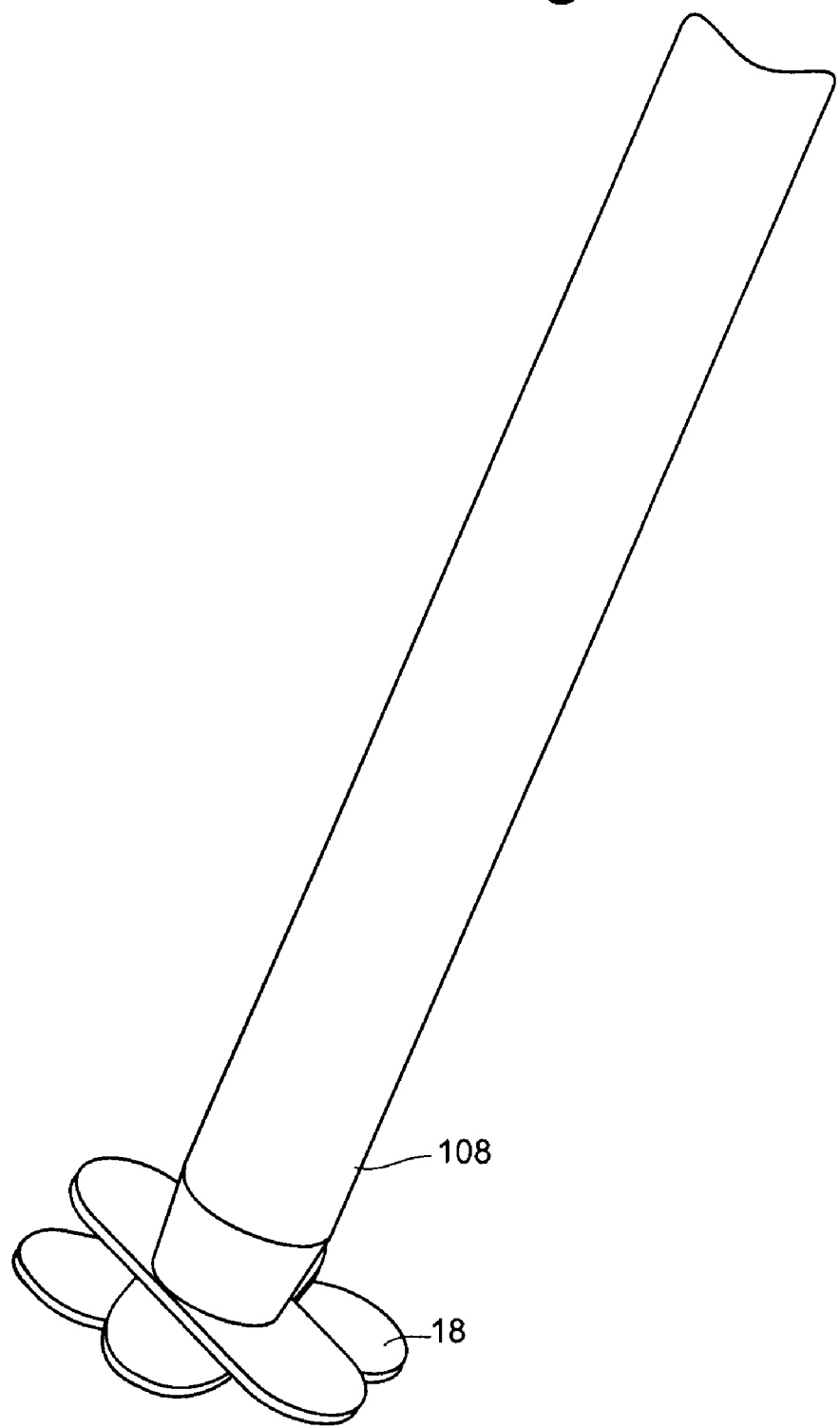
FIG. 15 is a perspective view of the distal end of a delivery tube and petals of the closure device in accordance with the invention.
Figure 16:
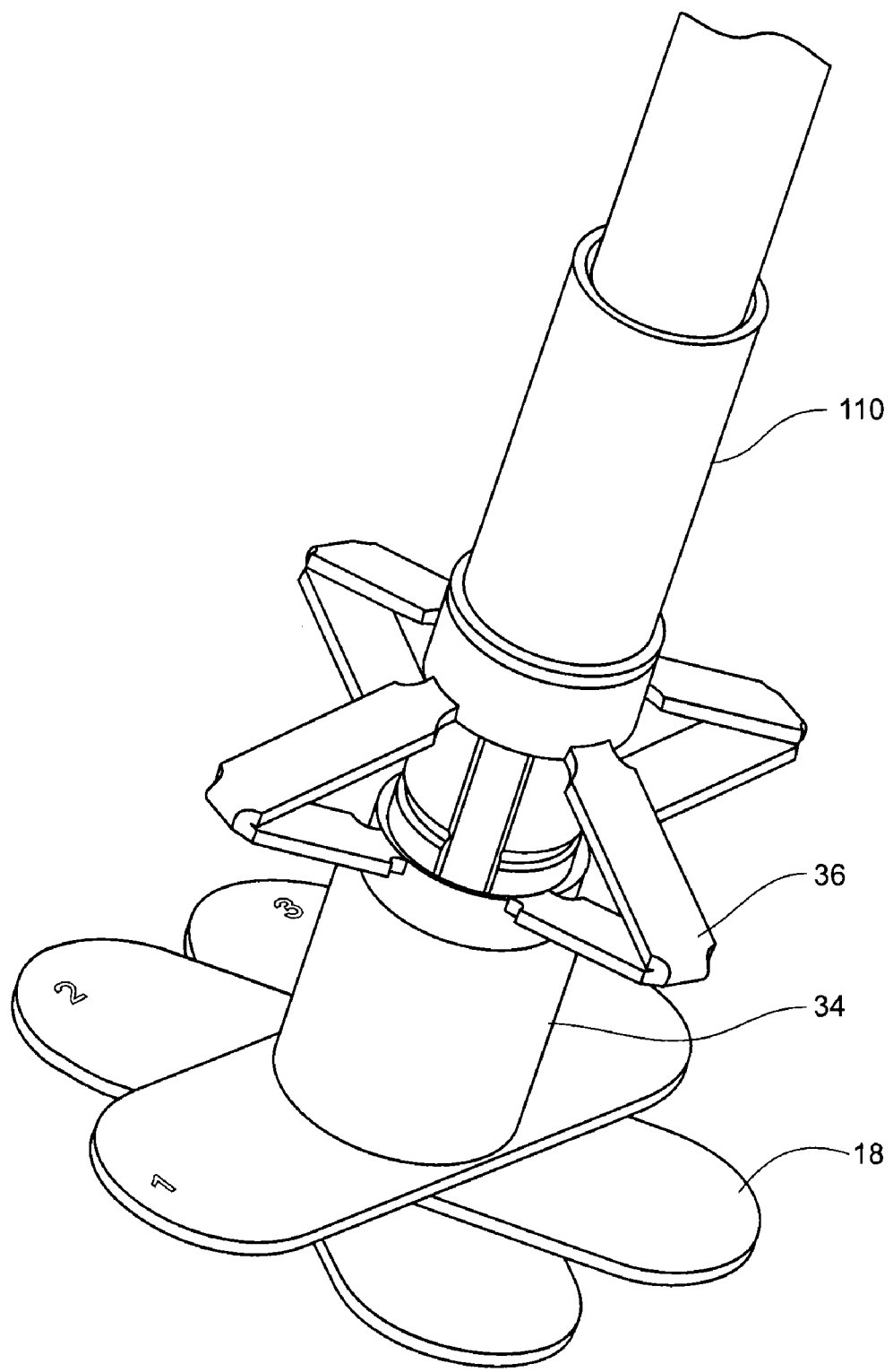
FIG. 16 is a perspective view of a closure device in the expanded state in accordance with the invention and the distal end of a delivery tube.

The physician then pulls filament 16 tight which pulls petals 18 into apposition against the inner wall of the blood vessel and optionally against delivery tube 108 as seen in FIG. 15. Next, the physician slightly advances deployment tube 110 while holding tension on filament 16. This action brings distal portion 48 and proximal portion 50 of expandable portion 36 toward each other while deforming expansion members 56 outwardly thus causing expansion portion 52 to expand outwardly, transversely relative to the long axis of expansion portion 52. At this time, expansion members 56 are deformed transversely and outwardly to engage the inner walls of the tissue tract and to resist any inward pulling by petals 18 via filament 16.

Figure 14:
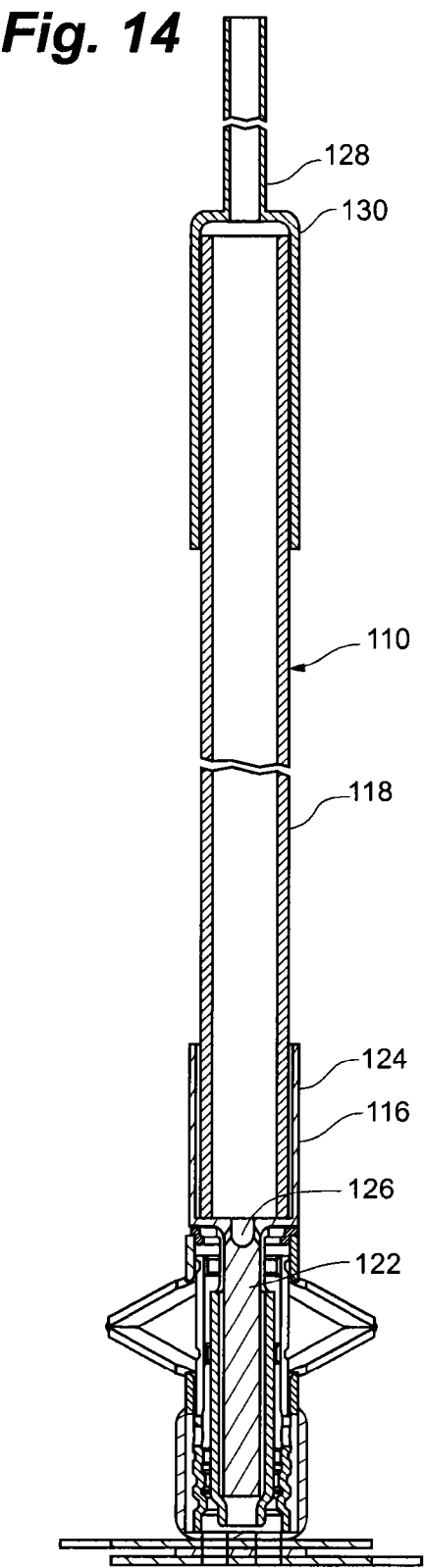
FIG. 14 is a sectional view taken along section lines 14-14 of FIG. 13.

As seen in FIGS. 3 and 14, simultaneously, probe 122 at the end of deployment tube 110 is engaged within wedge 66. Wedge 66 is forced into wedge receiver 68 while tension is still held on filament 16. As wedge 66 advances into wedge receiver 68, filament 16 is seized by friction and compression between nose portion 78 and sloped portion 80 of wedge 66 and retention ribs 90 of wedge receiver 68. Because of the relationship of proximal retention rib 92, intermediate retention rib 94 and distal retention rib 96, filament 16 is securely held between retention ribs 90 and wedge 66 thereby securing petals 18 against stem portion 34 and the blood vessel wall while preventing separation of petals 18 within the blood vessel lumen from stem portion 34 as well as from expandable portion 36. Deployment tube 110 is withdrawn from the tissue tract and can be discarded.

The combination of petals 18 and stem portion 34, and expandable portion 36 serve to substantially seal the incision in the blood vessel wall inhibiting any significant leakage. In particular, stem portion 34 is sized to largely fill the incision, whether the incision is circular or slit shaped, in order to facilitate sealing.

A physician may then push down on the percutaneous access site to compress the skin and underlying tissues between the blood vessel puncture and the skin puncture and cut off filament 16 as close as possible to the skin. When pressure is released, filament 16 then withdraws within the tissue tract.

Closure device 10 then is in place. Filament 16 is formed of a bioresorable material as discussed above; internal member 12 and external member 14 are formed of magnesium or another metal as discussed above. Closure device 10 then dissolves over a period of time while permitting healing of the puncture in the blood vessel and the tissue tract. As such, blood vessel leakage is prevented; ambulation of the patient is facilitated and healing proceeds in a quicker and more comfortable fashion for the patient.

The present invention may be embodied in other specific forms without departing from the spirit of the essential attributes thereof; therefore, the illustrated embodiments should be considered in all respects as illustrative and not restrictive, reference being made to the appended claims rather than to the foregoing description to indicate the scope of the invention.

The invention claimed is:

1. A closure device to be inserted at least partially through a blood vessel wall aperture in a blood vessel wall, the blood vessel having a lumen, the closure device comprising:

at least two metal petals, each petal being an independent structure separate from each other petal and having a length, a width and a thickness, the width and thickness being such that the at least two metal petals can be inserted through the blood vessel wall aperture and into the lumen of the blood vessel, the length and the width being such that the length and the width prevent withdrawal of the at least two metal petals from the blood vessel through the blood vessel wall aperture when the length of at least one of the two metal petals is generally aligned with the blood vessel wall, the at least two metal petals having alignment features that tend to urge the at least two metal petals into alignment relative to each other when the at least two metal petals are deployed within the blood vessel;

a metal expansion member that is alterable from an unexpanded state to an expanded state, which, when in the unexpanded state, is advanceable to a location near the blood vessel wall and which when in the expanded state is limited in movement relative to the blood vessel wall; and a bioabsorbable tensioning member that interconnects the at least two metal petals and the metal expansion member and that draws the petals and the metal expansion member toward each other upon being tensioned and that is securable to the metal expansion member to substantially maintain a relative positional relationship between the at least two metal petals and the metal expansion member upon being secured, whereby the at least two metal petals are positionable in the lumen adjacent to the blood vessel wall and the metal expansion member is limited in movement relative to the at least two metal petals and the at least two metal petals are stabilized in the blood vessel.

2. The closure device as claimed in claim 1, wherein the metal biodegrades within a living being in a period of time that permits biological repair of the blood vessel wall in and around the blood vessel aperture.

3. The closure device as claimed in claim 1, wherein a surface topography of at least one of the metal expansion member or the at least two metal petals is modified by roughening whereby biodegradation of at least part of the closure device is facilitated.

4. The closure device as claimed in claim 1, further comprising a chemical buffer whereby pH near at least part of the closure device is affected and whereby biodegradation of at least part of the closure device is facilitated.

5. The closure device as claimed in claim 1, further comprising a metal stem portion having a cross sectional dimension to fit within the blood vessel wall aperture in a relationship that inhibits the passage of fluid through the blood vessel wall aperture, the stem portion being located between the at least two petals and the expansion member.

6. The closure device as claimed in claim 1, wherein the bioabsorbable tensioning member comprises a filament that passes through each of the at least two metal petals and the expansion member and interfaces with the at least two metal petals in such a way that when the filament is tensioned the at least two metal petals are urged into an alignment wherein the length of the at least two metal petals is nonparallel.

7. The closure device as claimed in claim 1, wherein the alignment features comprise two apertures located in each of the at least two metal petals and the two apertures are differently oriented in each of the at least two metal petals such that when the apertures are aligned the at least two petals are offset from each other at angular intervals.

8. The closure device as claimed in claim 7, wherein the two apertures located in each of the at least two metal petals are differently angularly oriented relative to a long axis of each of the at least two metal petals such that when the apertures are aligned in the at least two petals the at least two petals are offset from each other at angular intervals.

9. The closure device as claimed in claim 1, wherein the alignment features comprise an aperture located in each of the at least two metal petals.

10. The closure device as claimed in claim 1, wherein the expansion member comprises a generally tubular structure having a deformable portion that deforms transversely upon longitudinal compression of the expansion member.

11. The closure device as claimed in claim 1, further comprising a locking portion that selectively secures the bioabsorbable tensioning member so that movement of the bioabsorbable tensioning member relative to the metal expansion member is inhibited.

12. The closure device as claimed in claim 11, the locking portion further comprising a wedge and a wedge receiver that the bioabsorbable tensioning member passes between, the wedge and the wedge receiver being shiftable relative to one another between a disengaged state and an engaged state, the disengaged state being such that the bioabsorbable tensioning member is movable relative to the metal expansion member, the engaged state being such that the bioabsorbable tensioning member is secured between the wedge and the wedge receiver to inhibit movement of the bioabsorbable tensioning member relative to the expansion member.

13. The closure device as claimed in claim 11, wherein the wedge, the wedge receiver or both are formed of metal.

14. The closure device as claimed in claim 13, wherein the metal consists essentially of magnesium.

15. The closure device as claimed in claim 1, further comprising an insertion assembly, the insertion assembly comprising a bypass tube, a delivery tube and a deployment tube.

16. The closure device as claimed in claim 15, the deployment tube further comprising an engagement feature at the distal end thereof, the engagement feature being structured to engage the metal expansion member and the deployment tube being structured to receive the bioabsorbable tensioning member therethrough, wherein the bioabsorbable tensioning member is movable through the deployment tube.

17. The closure device as claimed in claim 1, wherein the metal consists essentially of magnesium.

18. The closure device as claimed in claim 17, wherein the magnesium has a purity in a range from about 90.0 percent to about 99.99 percent.

19. The closure device as claimed in claim 17, wherein the magnesium is about 99.80 percent pure.

20. The closure device as claimed in claim 1, wherein the metal comprises magnesium alloyed with another metal.

21. The closure device as claimed in claim 20, wherein the magnesium is alloyed with iron.

22. The closure device as claimed in claim 20, wherein the magnesium is alloyed with manganese.

* * * * *